(12) United States Patent
Cholody et al.

(10) Patent No.: US 7,094,791 B2
(45) Date of Patent: Aug. 22, 2006

(54) DERIVATIVES OF 3-HYDROXY-PYRROLE-2,4-DICARBOXYLIC ACID AND USES THEREOF

(75) Inventors: Wieslaw M. Cholody, Frederick, MD (US); Valentina Petukhova, Rockville, MD (US); Sean O'Brien, Gaithersburg, MD (US); Norman Ohler, New Market, MD (US); Stanislaw Pikul, Germantown, MD (US)

(73) Assignee: Avalon Pharmaceuticals, Inc., Germantown, MD (US)

( * ) Notice: Subject to any disclaimer, the term of this patent is extended or adjusted under 35 U.S.C. 154(b) by 0 days.

(21) Appl. No.: 10/631,887

(22) Filed: Jul. 31, 2003

(65) Prior Publication Data

US 2005/0026991 A1    Feb. 3, 2005

(51) Int. Cl.
*A61K 31/445* (2006.01)
*C07D 207/00* (2006.01)

(52) U.S. Cl. .............. 514/326; 514/343; 514/423; 514/422; 548/530; 548/518; 546/208; 546/278.4

(58) Field of Classification Search ........... 548/530, 548/518; 546/208, 278.4; 514/326, 343, 514/423, 422
See application file for complete search history.

(56) References Cited

U.S. PATENT DOCUMENTS 6,750,239 B1 *    6/2004   Hale et al. ................ 514/406

OTHER PUBLICATIONS

Hale et al., 2003, CAS:138:170230.*

* cited by examiner

*Primary Examiner*—Kamal A. Salid
*Assistant Examiner*—Robert Shiao
(74) *Attorney, Agent, or Firm*—Elliot M. Olstein; Alan J. Grant

(57) ABSTRACT

Chemical agents of the general formula (I) and (II), such as derivatives of 3-hydroxy-pyrrole containing hydroxamic acid, and including salts thereof, that modulate levels of gene expression in cellular systems, including cancer cells, are disclosed, along with methods for preparing such agents, as well as pharmaceutical compositions containing such agents as active ingredients and methods of using these as therapeutic agents.

22 Claims, No Drawings

DERIVATIVES OF 3-HYDROXY-PYRROLE-2,4-DICARBOXYLIC ACID AND USES THEREOF

FIELD OF THE INVENTION

The present invention relates to chemical agents affecting levels of gene expression in cellular systems, including cancer cells, including methods of preparing them and using them as therapeutic agents, including anti-tumor agents.

BACKGROUND OF THE INVENTION

Screening assays for novel drugs are based on the response of model cell based systems in vitro to treatment with specific compounds. Various measures of cellular response have been utilized, including the release of cytokines, alterations in cell surface markers, activation of specific enzymes, as well as alterations in ion flux and/or pH. Some such screens rely on specific genes, such as oncogenes or tumor suppressors.

BRIEF SUMMARY OF THE INVENTION

In one aspect, the present invention relates to novel organic compounds, preferably derivatives of 3-hydroxypyrrole, that function as gene expression modulators for genes found in cancer cells, especially genes involved in misregulated signal transduction pathways typical of colon cancer.

In one embodiment of the present invention, the compounds disclosed herein up regulate genes found to be up regulated in normal cells (i.e., non-cancerous, especially normal colon cells) versus cancer cells, especially colon cancer cells, thereby producing an expression profile for said gene(s) that resembles the expression profile of said genes as found in normal cells. In another embodiment, the compounds disclosed herein are found to down regulate genes found to be up regulated in cancer cells, especially colon cancer cells, relative to normal (i.e., non-cancerous) cells thereby producing an expression profile for said gene(s) that resembles the expression profile of said genes as found in normal cells. In addition to activity in modulating a particular gene that may or may not have a major role in inducing or sustaining a cancerous condition, the agents disclosed herein also find value in regulating a set of genes whose combined activity is related to a disease condition, such as cancer, preferably colon cancer, most preferably adenocarcinoma of the colon. Thus, while an overall set of genes is modulated, the effect of modulating any subset of these may be disproportionately large or small with respect to the effect in ameliorating the overall disease process. Consequently, different disease conditions may rely on different subsets of genes to be active or inactive as a basis for the overall disease process.

In another embodiment, the present invention relates to novel organic compounds useful in treating a disease condition, such as cancer, arising in animals or human patients In other embodiments, the agents disclosed herein find use in combination with each other as well as with other agents, such as where a mixture of one or more of the agents of the present invention are given in combination or where one or more of the agents disclosed herein is given together with some other already known therapeutic agent, possibly as a means of potentiating the affects of such known therapeutic agent or vice versa.

The present invention also relates to methods of preventing or treating disease conditions, especially cancer, most especially colon cancer, by administering to a subject, such as a mammal, especially a human, a therapeutically active amount of one or more of the agents disclosed herein, including where such agents are given in combination with one or more known therapeutic agents.

DEFINITIONS

The following is a list of definitions for terms used herein.

"Acyl" or "carbonyl" is a radical formed by removal of the hydroxy from a carboxylic acid (i.e., R—C(=O)—). Preferred acyl groups include (for example) acetyl, formyl, and propionyl.

"Alkyl" is a saturated hydrocarbon chain having 1 to 15 carbon atoms, preferably 1 to 10, more preferably 1 to 4 carbon atoms. "Alkene" is a hydrocarbon chain having at least one (preferably only one) carbon-carbon double bond and having 2 to 15 carbon atoms, preferably 2 to 10, more preferably 2 to 4 carbon atoms. "Alkyne" is a hydrocarbon chain having at least one (preferably only one) carbon-carbon triple bond and having 2 to 15 carbon atoms, preferably 2 to 10, more preferably 2 to 4 carbon atoms. Alkyl, alkene and alkyne chains (referred to collectively as "hydrocarbon chains") may be straight or branched and may be unsubstituted or substituted. Preferred branched alkyl, alkene and alkyne chains have one or two branches, preferably one branch. Preferred chains are alkyl. Alkyl, alkene and alkyne hydrocarbon chains each may be unsubstituted or substituted with from 1 to 4 substituents; when substituted, preferred chains are mono-, di-, or tri-substituted. Alkyl, alkene and alkyne hydrocarbon chains each may be substituted with halo, hydroxy, aryloxy (e.g., phenoxy), heteroaryloxy, acyloxy (e.g., acetoxy), carboxy, aryl (e.g., phenyl), heteroaryl, cycloalkyl, heterocycloalkyl, spirocycle, amino, amido, acylamino, keto, thioketo, cyano, or any combination thereof. Preferred hydrocarbon groups include methyl, ethyl, propyl, isopropyl, butyl, vinyl, allyl, butenyl, and exomethylenyl.

Also, as referred to herein, a "lower" alkyl, alkene or alkyne moiety (e.g., "lower alkyl") is a chain comprised of 1 to 6, preferably from 1 to 4, carbon atoms in the case of alkyl and 2 to 6, preferably 2 to 4, carbon atoms in the case of alkene and alkyne.

"Alkoxy" is an oxygen radical having a hydrocarbon chain substituent, where the hydrocarbon chain is an alkyl or alkenyl (i.e., —O-alkyl or —O-alkenyl). Preferred alkoxy groups include (for example) methoxy, ethoxy, propoxy and allyloxy.

"Aryl" is an aromatic hydrocarbon ring. Aryl rings are monocyclic or fused bicyclic ring systems. Monocyclic aryl rings contain 6 carbon atoms in the ring. Monocyclic aryl rings are also referred to as phenyl rings. Bicyclic aryl rings contain from 8 to 17 carbon atoms, preferably 9 to 12 carbon atoms, in the ring. Bicyclic aryl rings include ring systems wherein one ring is aryl and the other ring is aryl, cycloalkyl, or heterocycloalkyl. Preferred bicyclic aryl rings comprise 5-, 6- or 7-membered rings fused to 5-, 6-, or 7-membered rings. Aryl rings may be unsubstituted or substituted with from 1 to 4 substituents on the ring. Aryl may be substituted with halo, cyano, nitro, hydroxy, carboxy, amino, acylamino, alkyl, heteroalkyl, haloalkyl, phenyl, aryloxy, alkoxy, heteroalkyloxy, carbamyl, haloalkyl, methylenedioxy, heteroaryloxy, or any combination thereof. Preferred aryl rings include naphthyl, tolyl, xylyl, and phenyl. The most preferred aryl ring radical is phenyl.

"Aryloxy" is an oxygen radical having an aryl substituent (i.e., —O-aryl). Preferred aryloxy groups include (for example) phenoxy, napthyloxy, methoxyphenoxy, and methylenedioxyphenoxy.

"Cycloalkyl" is a saturated or unsaturated hydrocarbon ring. Cycloalkyl rings are not aromatic. Cycloalkyl rings are monocyclic, or are fused, spiro, or bridged bicyclic ring systems. Monocyclic cycloalkyl rings contain from about 3 to about 9 carbon atoms, preferably from 3 to 7 carbon atoms, in the ring. Bicyclic cycloalkyl rings contain from 7 to 17 carbon atoms, preferably from 7 to 12 carbon atoms, in the ring. Preferred bicyclic cycloalkyl rings comprise 4-, 5-, 6- or 7-membered rings fused to 5-, 6-, or 7-membered rings. Cycloalkyl rings may be unsubstituted or substituted with from 1 to 4 substituents on the ring. Cycloalkyl may be substituted with halo, cyano, alkyl, heteroalkyl, haloalkyl, phenyl, keto, hydroxy, carboxy, amino, acylamino, aryloxy, heteroaryloxy, or any combination thereof. Preferred cycloalkyl rings include cyclopropyl, cyclopentyl, and cyclohexyl.

"Halo" or "halogen" is fluoro, chloro, bromo or iodo. Preferred halo are fluoro, chloro and bromo; more preferred typically are chloro and fluoro, especially fluoro.

"Haloalkyl" is a straight, branched, or cyclic hydrocarbon substituted with one or more halo substituents. Preferred are $C_1$–$C_{12}$ haloalkyls; more preferred are $C_1$–$C_6$ haloalkyls; still more preferred still are $C_1$–$C_3$ haloalkyls. Preferred halo substituents are fluoro and chloro. The most preferred haloalkyl is trifluoromethyl.

"Heteroatom" is a nitrogen, sulfur, or oxygen atom. Groups containing more than one heteroatom may contain different heteroatoms.

"Heteroalkyl" is a saturated or unsaturated chain containing carbon and at least one heteroatom, wherein no two heteroatoms are adjacent. Heteroalkyl chains contain from 2 to 15 member atoms (carbon and heteroatoms) in the chain, preferably 2 to 10, more preferably 2 to 5. For example, alkoxy (i.e., —O-alkyl or —O-heteroalkyl) radicals are included in heteroalkyl. Heteroalkyl chains may be straight or branched. Preferred branched heteroalkyl have one or two branches, preferably one branch. Preferred heteroalkyl are saturated. Unsaturated heteroalkyl have one or more carbon-carbon double bonds and/or one or more carbon-carbon triple bonds. Preferred unsaturated heteroalkyls have one or two double bonds or one triple bond, more preferably one double bond. Heteroalkyl chains may be unsubstituted or substituted with from 1 to 4 substituents. Preferred substituted heteroalkyl are mono-, di-, or tri-substituted. Heteroalkyl may be substituted with lower alkyl, haloalkyl, halo, hydroxy, aryloxy, heteroaryloxy, acyloxy, carboxy, monocyclic aryl, heteroaryl, cycloalkyl, heterocycloalkyl, spirocycle, amino, acylamino, amido, keto, thioketo, cyano, or any combination thereof.

"Heteroaryl" is an aromatic ring containing carbon atoms and from 1 to about 6 heteroatoms in the ring. Heteroaryl rings are monocyclic or fused bicyclic ring systems. Monocyclic heteroaryl rings contain from about 5 to about 9 member atoms (carbon and heteroatoms), preferably 5 or 6 member atoms, in the ring. Bicyclic heteroaryl rings contain from 8 to 17 member atoms, preferably 8 to 12 member atoms, in the ring. Bicyclic heteroaryl rings include ring systems wherein one ring is heteroaryl and the other ring is aryl, heteroaryl, cycloalkyl, or heterocycloalkyl. Preferred bicyclic heteroaryl ring systems comprise 5-, 6- or 7-membered rings fused to 5-, 6-, or 7-membered rings. Heteroaryl rings may be unsubstituted or substituted with from 1 to 4 substituents on the ring. Heteroaryl may be substituted with halo, cyano, nitro, hydroxy, carboxy, amino, acylamino, alkyl, heteroalkyl, haloalkyl, phenyl, alkoxy, aryloxy, heteroaryloxy, or any combination thereof. Preferred heteroaryl rings include, but are not limited to, the following:

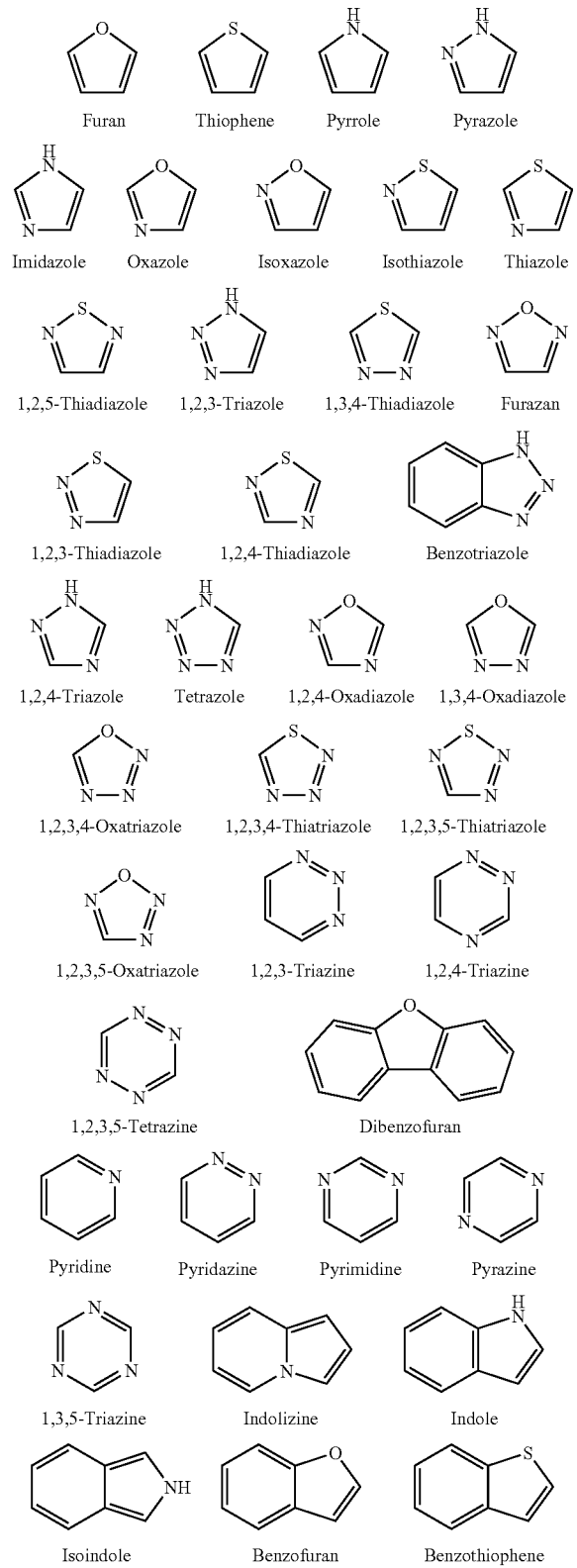

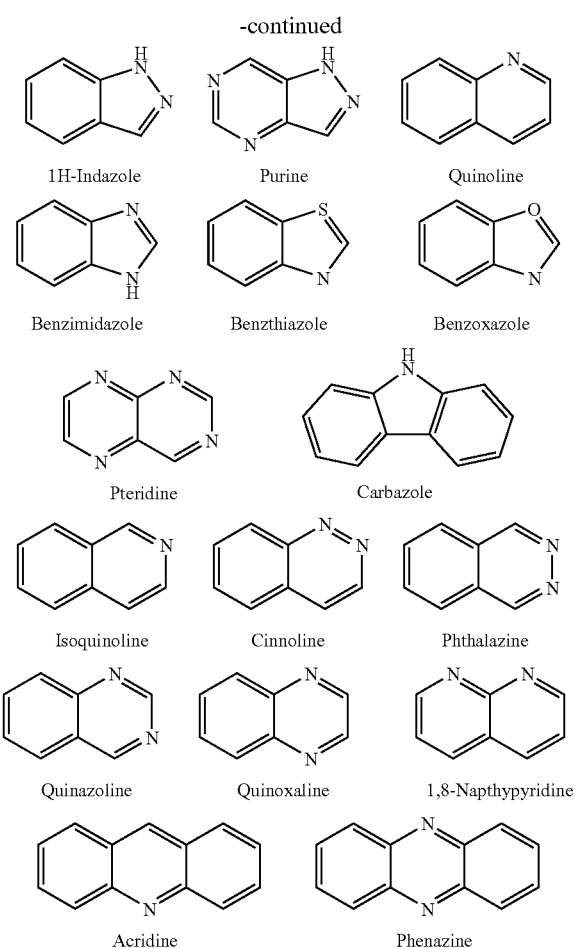

"Heteroaryloxy" is an oxygen radical having a heteroaryl substituent (i.e., —O-heteroaryl). Preferred heteroaryloxy groups include (for example) pyridyloxy, furanyloxy, (thiophene)oxy, (oxazole)oxy, (thiazole)oxy, (isoxazole)oxy, pyrmidinyloxy, pyrazinyloxy, and benzothiazolyloxy.

"Heterocycloalkyl" is a saturated or unsaturated ring containing carbon atoms and from 1 to about 4 (preferably 1 to 3) heteroatoms in the ring. Heterocycloalkyl rings are not aromatic. Heterocycloalkyl rings are monocyclic, or are fused, bridged, or spiro bicyclic ring systems. Monocyclic heterocycloalkyl rings contain from about 3 to about 9 member atoms (carbon and heteroatoms), preferably from 5 to 7 member atoms, in the ring. Bicyclic heterocycloalkyl rings contain from 7 to 17 member atoms, preferably 7 to 12 member atoms, in the ring. Bicyclic heterocycloalkyl rings contain from about 7 to about 17 ring atoms, preferably from 7 to 12 ring atoms. Bicyclic heterocycloalkyl rings may be fused, spiro, or bridged ring systems. Preferred bicyclic heterocycloalkyl rings comprise 5-, 6- or 7-membered rings fused to 5-, 6-, or 7-membered rings. Heterocycloalkyl rings may be unsubstituted or substituted with from 1 to 4 substituents on the ring. Heterocycloalkyl may be substituted with halo, cyano, hydroxy, carboxy, keto, thioketo, amino, acylamino, acyl, amido, alkyl, heteroalkyl, haloalkyl, phenyl, alkoxy, aryloxy or any combination thereof. Preferred substituents on heterocycloalkyl include halo and haloalkyl. Preferred heterocycloalkyl rings include, but are not limited to, the following:

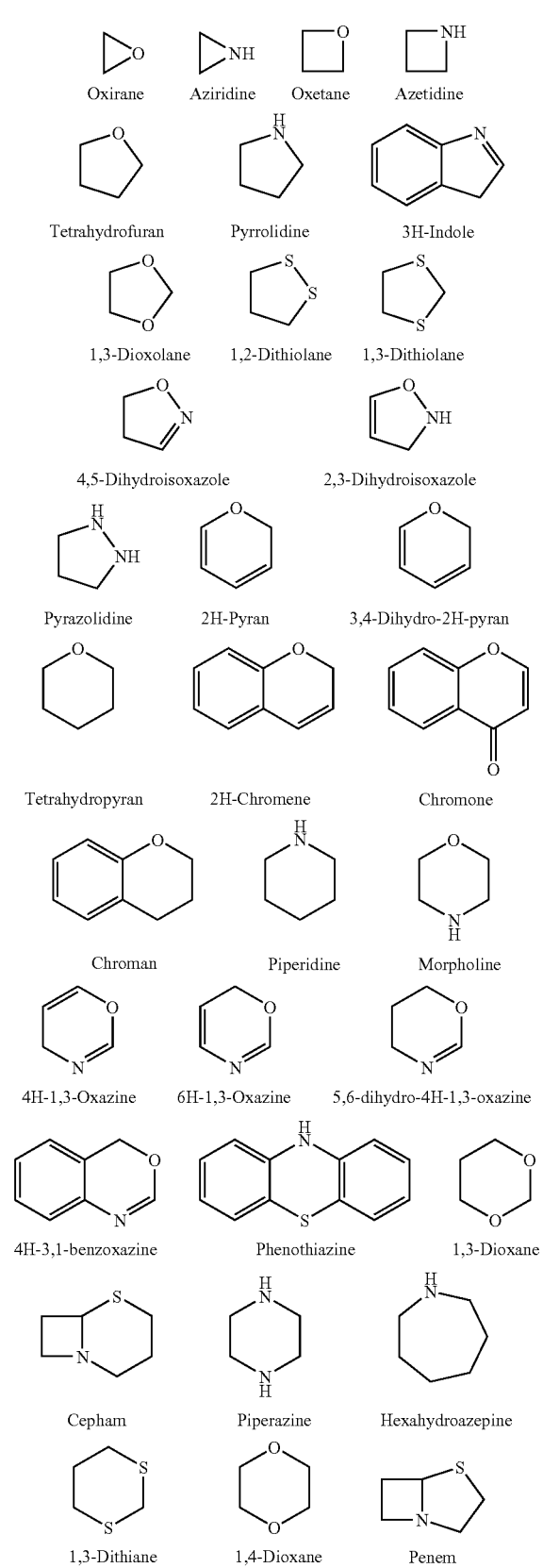

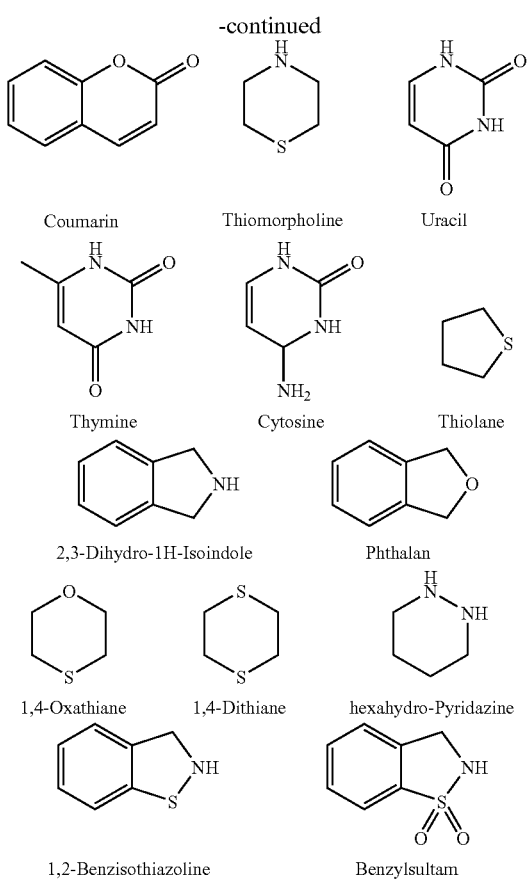

Coumarin   Thiomorpholine   Uracil

Thymine   Cytosine   Thiolane 2,3-Dihydro-1H-Isoindole   Phthalan 1,4-Oxathiane   1,4-Dithiane   hexahydro-Pyridazine 1,2-Benzisothiazoline   Benzylsultam While alkyl, heteroalkyl, cycloalkyl, and heterocycloalkyl groups may be substituted with hydroxy, amino, and amido groups as stated above, the following are not envisioned in the invention:

Enols (OH attached to a carbon bearing a double bond).

Amino groups attached to a carbon bearing a double bond (except for vinylogous amides).

More than one hydroxy, amino, or amido attached to a single carbon (except where two nitrogen atoms are attached to a single carbon atom and all three atoms are member atoms within a heterocycloalkyl ring).

Hydroxy, amino, or amido attached to a carbon that also has a heteroatom attached to it.

Hydroxy, amino, or amido attached to a carbon that also has a halogen attached to it.

A "pharmaceutically-acceptable salt" is a cationic salt formed at any acidic (e.g., carboxylic acid) group, or an anionic salt formed at any basic (e.g., amino) group. Many such salts are known in the art, as described in World Patent Publication 87/05297, Johnston et al., published Sep. 11, 1987 incorporated by reference herein. Preferred cationic salts include the alkali metal salts (such as sodium and potassium), and alkaline earth metal salts (such as magnesium and calcium) and organic salts. Preferred anionic salts include the halides (such as chloride salts), sulfonates, carboxylates, phosphates, and the like.

Such salts are well understood by the skilled artisan, and the skilled artisan is able to prepare any number of salts given the knowledge in the art. Furthermore, it is recognized that the skilled artisan may prefer one salt over another for reasons of solubility, stability, formulation ease and the like. Determination and optimization of such salts is within the purview of the skilled artisan's practice.

A "solvate" is a complex formed by the combination of a solute (e.g., a metalloprotease inhibitor) and a solvent (e.g., water). See J. Honig et al., *The Van Nostrand Chemist's Dictionary*, p. 650 (1953). Pharmaceutically-acceptable solvents used according to this invention include those that do not interfere with the biological activity of the metalloprotease inhibitor (e.g., water, ethanol, acetic acid, N,N-dimethylformamide and others known or readily determined by the skilled artisan).

The terms "optical isomer", "stereoisomer", and "diastereomer" have the accepted meanings (see, e.g., *Hawley's Condensed Chemical Dictionary*, 11th Ed.). The illustration of specific protected forms and other derivatives of the compounds of the instant invention is not intended to be limiting. The application of other useful protecting groups, salt forms, etc. is within the ability of the skilled artisan.

DETAILED DESCRIPTION OF THE INVENTION

The present invention relates to small molecule compounds as potential anticancer drugs and relies on the concept that for each specific tumor type, a unique signature set of genes, that are differentially expressed in tumor cells can be established. The relatively small signature set, containing 10–30 genes, allows for easy, high throughput screening for compounds that can cause significant changes in the expression of misregulated genes of tumor cells. Part of the present effort to provide new diversified compounds for high throughput gene expression screening involved the design and synthesis of a number of novel derivatives of 3-hydroxy-pyrrole, which contain a hydroxamic acid moiety directly connected to the pyrrole ring. Gene expression screening and subsequent cytotoxicity screening revealed that some of the compounds possess biological activity. Consequent, more detailed structure-activity relationship studies led to the discovery of compounds of formula I as new small molecule agents having antineoplastic activity.

This present invention provides a new class of substituted pyrroles, containing hydroxamic acid moiety attached directly to the heterocycle ring, and their use as antineoplastic agents. The compounds of the invention have the general structure as follows:

Formula I

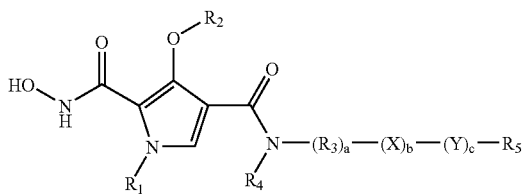

Formula II

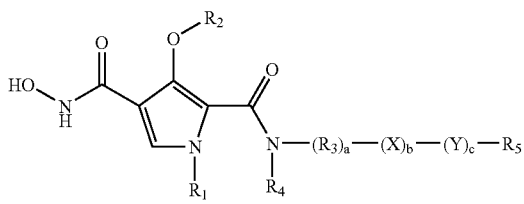

In preferred embodiments, the pyrrole nitrogen may be located at different positions of the pyrrole ring system.

The present invention relates to antitumor agents capable of modulating the expression of specified genes, or sets of genes, found to be active, or possibly inactive or functioning at a low degree of expression, relative to normal cells.

In particular, the compounds are found to affect expression of genes from a colon cancer signature gene set. Expression levels of such genes are markedly altered in cells derived from human colon cancer tissue, especially adenocarcinoma, as compared to cells derived from healthy individuals. Because the compounds disclosed herein can affect gene expression they may be useful for the treatment of many types of cancers, as well as colon cancer. Additionally, the compounds may be useful for the treatment of a variety of other conditions associated with changes in levels of gene expression.

The ability of compounds described herein to affect gene expression is a novel observation, and such activity could not be predicted based on information available in the public domain. Compounds with this activity may have the ability to affect the cell cycle of the transformed cells (cancer cells) and selectively induce them back into a normal state or into apoptosis (programmed cell death). Therefore, the compounds may have a significant therapeutic potential for the treatment of cancer and other conditions associated with changes in levels of gene expression.

In accordance with the present invention, the compounds disclosed herein have been shown to modulate gene expression using model cellular systems employing the HT29 and Colo205 colon tumor cell lines (used for the data reported in Table 1). In such assays, primary cells, or tissue samples, are maintained in growth media and are treated with compounds at a single concentration or at a range of concentrations. At specific times after treatment, cellular RNAs are isolated from the treated cells, primary cells or tumors, which RNAs are indicative of expression of selected genes, including, but not limited to, the genes used herein. The cellular RNA is then divided and subjected to analysis that detects the presence and/or quantity of specific RNA transcripts, which transcripts may then be amplified for detection purposes using standard methodologies, such as, for example, reverse transcriptase polymerase chain reaction (RT-PCR), etc. The presence or absence, or levels, of specific RNA transcripts are determined from these measurements and a metric derived for the type and degree of response of the sample to the treated compound compared to control samples. One such procedure is illustrated by example 8 herein.

The characteristic genes, or signature sets of genes and gene sequences whose expression is modulated by the agents disclosed herein are ones that are linked to, or used to characterize, the cancerous, or non-cancerous, status of the cells, or tissues, to be tested. They may also be linked to other diseases disclosed herein. Thus, the compounds disclosed herein include novel anti-neoplastic agents that effect alteration of expression of small sets of characteristic, or indicator, or signature genes in specific model systems. In accordance with the present invention, analogs of such compounds are routinely produced by combinatorial methods and then readily assayed with a variety of cell lines or with primary samples from tumors maintained in vitro under suitable culture conditions for varying periods of time, or in situ in suitable animal models.

In accordance with the present invention, certain genes have been identified that are expressed at levels in cancer cells that are different than the expression levels in non-cancer cells. In one instance, the identified genes are expressed at higher levels in cancer cells than in normal cells. In another instance, the identified genes are expressed at lower levels in cancer cells as compared to normal cells.

In accordance with the foregoing, the therapeutic, including anti-neoplastic, agents disclosed herein are screened using a method comprising the steps of:

(a) contacting a cell with a chemical agent to be tested for antineoplastic activity, and (b) determining a change in expression of at least one gene of interest, preferably a gene used to accumulate the data of Table 1. In such assay, a change in expression is indicative of anti-neoplastic activity.

Thus, in determining the therapeutic ability of the agents disclosed herein, a set of 11 genes over- or under-expressed in colon cancer cells were used to determine the ability of compounds of the invention to modulate activity of this gene set. Other gene sets related to other diseases, including other cancers, can likewise be conveniently used for such screenings.

In a specific embodiment, the compounds of the invention have the general structure of Formula (I) or Formula (II)

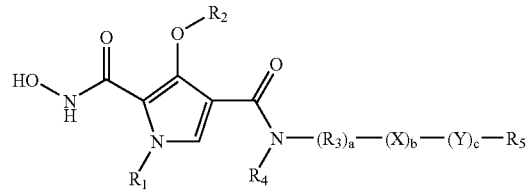

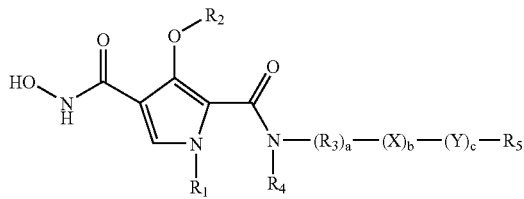

wherein:

$R_1$ is selected from H, substituted and unsubstituted alkyl, substituted and unsubstituted heteroalkyl, substituted and unsubstituted aryl, substituted and unsubstituted arylalkyl, substituted and unsubstituted heteroaryl, substituted and unsubstituted heteroarylalkyl, substituted and unsubstituted cycloalkyl, and substituted and unsubstituted heterocycloalkyl;

$R_2$ is selected from H, substituted and unsubstituted alkyl, substituted and unsubstituted alkenyl, substituted and unsubstituted alkynyl, substituted and unsubstituted heteroalkyl, substituted and unsubstituted haloalkyl, substituted and unsubstituted aryl, substituted and unsubstituted arylalkyl, substituted and unsubstituted heteroaryl, substituted and unsubstituted heteroarylalkyl, substituted and unsubstituted cycloalkyl, and substituted and unsubstituted heterocycloalkyl;

$R_3$ is selected from a substituted and unsubstituted alkyl or a substituted and unsubstituted heteroalkyl;

$R_4$ is selected from H, substituted and unsubstituted alkyl, substituted and unsubstituted heteroalkyl, substituted and unsubstituted aryl, substituted and unsubstituted arylalkyl, substituted and unsubstituted heteroaryl, substituted and unsubstituted heteroarylalkyl, substituted and unsubstituted cycloalkyl, and substituted and unsubstituted heterocycloalkyl;

$R_3$ and $R_4$ can be connected together to form a 4, 5, 6 or 7-member heterocylce;

$R_5$ is selected from H, substituted and unsubstituted alkyl, substituted and unsubstituted heteroalkyl, substituted and unsubstituted aryl, substituted and unsubstituted arylalkyl, substituted and unsubstituted heteroaryl, substituted and unsubstituted heteroarylalkyl, substituted and unsubstituted cycloalkyl, and substituted and unsubstituted heterocycloalkyl;

X and Y are independently selected from substituted and unsubstituted alkyl, substituted and unsubstituted alkenyl, substituted and unsubstituted alkynyl, substituted and unsubstituted heteroalkyl, substituted and unsubstituted haloalkyl, substituted and unsubstituted aryl, substituted and unsubstituted arylalkyl, substituted and unsubstituted heteroaryl, substituted and unsubstituted heteroarylalkyl, substituted and unsubstituted cycloalkyl, substituted and unsubstituted heterocycloalkyl, $CO_2$, CO and $SO_2$, wherein a, b and c are each independently 0 or 1, and including pharmaceutically acceptable salts thereof.

In a preferred embodiment of the compounds of the invention, $R_1$ is —H, lower substituted and unsubstituted alkyl, substituted and unsubstituted benzyl, substituted and unsubstituted alkoxybenzyl, substituted and unsubstituted dialkylamino alkyl, most preferably wherein $R_1$ is methyl or substituted and unsubstituted benzyl.

In another preferred embodiment of the compounds of the invention, $R_2$ is —H, lower substituted and unsubstituted alkyl, substituted and unsubstituted arylalkyl, or substituted and unsubstituted heteroarylalkyl, most preferably wherein $R_2$ is substituted or unsubstituted arylalkyl with 0–4 substituents selected from alkoxy, halo (F, Cl, Br), CN, 2,4-di-Cl, 3,4-di-Cl, 2,6-di-Cl, 3,4-di-F, and the like.

In an additional preferred embodiment of the compounds of the invention, $R_3$ is selected from substituted and unsubstituted alkyl or substituted and unsubstituted heteroalkyl.

In a further preferred embodiment of the compounds of the invention, $R_4$ is —H or substituted or unsubstituted lower alkyl, most preferably wherein $R_4$ and $R_3$ form a 4, 5, 6 or 7-member heterocylce with 1–3 heteroatoms.

In a still further preferred embodiment of the compounds of the invention, the heterocylic ring is piperazine, homopiperazine or pyrrolidine.

In a yet further preferred embodiment of the compounds of the invention, X is alkyl, heterolakyl, heterocycle, aryl or heteroaryl, more preferably wherein X is a 4, 5, 6 or 7-member heterocylce with 1–3 heteroatoms, and most preferably wherein X is piperidine.

In a yet still further preferred embodiment of the compounds of the invention, Y is bond (meaning that c is 0), alkyl, heterocycle, aryl, heteroaryl or COO.

In one embodiment of the compounds of the invention, Y is a 4, 5, 6 or 7-member heterocylce with 1–3 heteroatoms, or wherein Y is COO.

In another embodiment of the compounds of the invention, $R_5$ is —H, substituted and unsubstituted alkyl, substituted and unsubstituted heteroalkyl, substituted and unsubstituted aryl, substituted and unsubstituted heteroaryl, or substituted and unsubstituted heterocycle, preferably wherein $R_5$ is aryl or substituted aryl and most preferably wherein $R_5$ is phenyl or benzyl.

In another aspect, the present invention relates to compositions of any of the compounds of the invention, preferably wherein such compound is present in a pharmaceutically acceptable carrier and in a therapeutically effective amount. Such compositions will generally comprise an amount of such compound that is not toxic (i.e., an amount that is safe for therapeutic uses).

In accordance with the foregoing, the present invention is directed to use of the compounds of the invention as active ingredients for medicaments, in particular for medicaments useful for the treatment of tumors. The compounds of the invention will thus be present in pharmaceutical compositions containing compounds of formula I as active ingredients, in admixture with pharmaceutically acceptable vehicles and excipients, which includes any pharmaceutical agent that does not itself induce the production of antibodies harmful to the individual receiving the composition, and which may be administered without undue toxicity. Pharmaceutically acceptable carriers include, but are not limited to, liquids such as water, saline, glycerol and ethanol, and the like, including carriers useful in forming sprays for nasal and other respiratory tract delivery or for delivery to the ophthalmic system. A thorough discussion of pharmaceutically acceptable carriers, diluents, and other excipients is presented in REMINGTON'S PHARMACEUTICAL SCIENCES (Mack Pub. Co., N.J. current edition). Use of such carriers is well known to those skilled in the art and will not be discussed further herein.

Also in accordance with the foregoing, the present invention relates to a method for preventing or treating a disease associated with a change in levels of expression of particular sets of genes in a mammal comprising administering to said mammal an effective amount of a compound of the invention.

In another aspect, the present invention relates to a method for preventing or treating a disorder modulated by altered gene expression, wherein the disorder is selected from the group consisting of cancer, cardiovascular disorders, arthritis, osteoporosis, inflammation, periodontal disease and skin disorders, comprising administering to a mammal in need of such treatment or prevention a therapeutically effective amount of a compound of the invention.

In a preferred embodiment thereof, the disorder is cancer, more preferably colon cancer, most preferably adenocarcinoma, and the treatment prevents, arrests or reverts tumor growth, metastasis or both.

The compounds of the invention will commonly exert a therapeutic effect by modulation of one or more genes found in a cell, especially a mammalian cell, such as a cancer cell, preferably colon cancer and most preferably adenocarcinoma. Thus, a compound, or compounds, of the invention can be used to determine or demarcate a set of genes by determining modulation of such set of genes by one or more compounds of the invention. For example, where a set of genes is found to be up-regulated in cancer cells versus otherwise normal cells, especially normal cells of the same tissue or organ as the cancer cells, a set of genes can be determined by their common property of being modulated (based on a change in expression of the genes, such as a change in rate or amount of RNA transcribed or the amount of polypeptide produced by said expression) by contacting such genes, or a cell containing such genes, with one or more of the compounds of the invention. The extent of such modulation may, of course, be related to the amount of said compound, or compounds, used in the contacting. Such modulation may include the increased expression of all the determined genes (i.e., the genes of the set), the decreased expression of all genes of the set, or the increase in expression of some of the genes of the set and decreased expression of others. Thus, a gene not modulated by the test compound (the compound used in contacting the genes or cell containing them) is not considered a member of the set.

Thus, the present invention relates to a gene set wherein expression of each member of said gene set is modulated as a result of contacting said gene set with a compound of the invention. In specific embodiments, expression of each member of said gene set is increased as a result of said contacting or is decreased as a result of said contacting. In another preferred embodiment, the gene set is present in a cell. Such a gene set will commonly be related to a specific disease process, such as a set of genes all of which are modulated by a compound of the invention wherein such compound has a specific therapeutic effect, such as being an anti-neoplastic agent.

In another aspect, the present invention relates to a method for identifying an agent that modulates the expression of a gene set of the invention, comprising:

(a) contacting, or otherwise using, a compound, such as a test compound, a test system, such as a source of genes or polynucleotides, for example, those found to be related to a given disease or disorder, or a set that is modulated by a given compound, or group of compounds, especially where these are found in a cell, so that the cell represents the test system, containing one or more polynucleotides corresponding to each of the members of the gene set of the invention under conditions wherein the members of said gene set are being expressed;

(b) determining a change in expression of each of said one or more polynucleotides of step (a) as a result of said treatment;

wherein said change in expression of step (b) indicates modulation of the members of said gene set by the test compound thereby identifying a test compound that modulates the expression of said gene set.

In one embodiment, the cell may be a naturally derived cell that contains genes of a gene set or may be a recombinant cell engineered to comprise the genes or polynucleotides of the gene set. In an alternative embodiment, the test system may comprise the genes or polynucleotides in a cell-free system.

As used herein, "corresponding genes" or "corresponding polynucleotides" or "polynucleotides corresponding to genes" refers to polynucleotides and/or genes that encode an RNA that is at least 90% identical, preferably at least 95% identical, most preferably at least 98% identical, and especially identical, to an RNA encoded by one of the genes disclosed herein in Tables 8 and 9. Such genes will also encode the same polypeptide sequence, but may include differences in such amino acid sequences where such differences are limited to conservative amino acid substitutions, such as where the same overall three dimensional structure, is maintained. A "corresponding gene" includes splice variants thereof.

Because a polynucleotide or gene used in the methods of the invention "corresponds to" a gene present in one of the gene sets of the invention, such as genes identified in Tables 8 and 9, such polynucleotide or gene encodes an RNA (processed or unprocessed, including naturally occurring splice variants and alleles) that is at least 90% identical, preferably at least 95% identical, most preferably at least 98% identical to, and especially identical to, an RNA that would be encoded by, or be complementary to, such as by hybridization with, a gene of Table 8 or 9, or genes of any gene set identified according to the invention. Polynucleotides encoding the same proteins as any of these genes, regardless of the percent identity of the sequences of such genes and/or polynucleotides, are also specifically contemplated by any of the methods of the present invention. The polynucleotides used in the methods of the invention also include any open reading frames, as defined herein, present therein. As used herein, the term "open reading frame" (or ORF) means a series of triplets coding for amino acids without any termination codons and is a sequence (potentially) translatable into protein.

The polynucleotides useful in the methods of the invention may be genomic in nature and thus represent the sequence of an actual gene, such as a human gene, or may be a cDNA sequence derived from a messenger RNA (mRNA) and thus represent contiguous exonic sequences derived from a corresponding genomic sequence, or they may be wholly synthetic in origin for purposes of practicing the processes of the invention. Because of the processing that may take place in transforming the initial RNA transcript into the final mRNA, the sequences disclosed herein may represent less than the full genomic sequence. They may also represent sequences derived from ribosomal and transfer RNAs. Consequently, the gene as present in the cell (and representing the genomic sequence) and the polynucleotide transcripts disclosed herein, including cDNA sequences, may be identical or may be such that the cDNAs contain less than the full genomic sequence. Such genes and cDNA sequences are still considered "corresponding sequences" (as defined elsewhere herein) because they both encode the same or related RNA sequences (i.e., related in the sense of being splice variants or RNAs at different stages of processing). Thus, by way of non-limiting example only, a gene that encodes an RNA transcript, which is then processed into a shorter mRNA, is deemed to encode both such RNAs and therefore encodes an RNA complementary to (using the usual Watson-Crick complementarity rules), or that would otherwise be encoded by, a cDNA (for example, a sequence as disclosed herein). Thus, the sequences disclosed herein correspond to genes contained in the cancerous cells (here, breast cancer) and are used to determine gene activity or expression because they represent the same sequence or are complementary to RNAs encoded by the gene. Such a gene also includes different alleles and splice variants that may occur in the cells used in the methods of the invention, such as where recombinant cells are used to assay for anti-neoplastic agents and such cells have been engineered to express a polynucleotide as disclosed herein, including cells that have been engineered to express such polynucleotides at a higher level than is found in non-engineered cancerous cells or where such recombinant cells express such polynucleotides only after having been engineered to do so. Such engineering includes genetic engineering, such as where one or more of the polynucleotides disclosed herein has been inserted into the genome of such cell or is present in a vector.

Such cells, especially mammalian cells, may also be engineered to express on their surfaces one or more of the polypeptides of the invention for testing with antibodies or other agents capable of masking such polypeptides and thereby removing the cancerous nature of the cell. Such engineering includes both genetic engineering, where the genetic complement of the cells is engineered to express the polypeptide, as well as non-genetic engineering, whereby the cell has been physically manipulated to incorporate a polypeptide of the invention in its plasma membrane, such as by direct insertion using chemical and/or other agents to achieve this result.

In a preferred embodiment of such method, the determined change in expression is a decrease in expression of said one or more polynucleotides or a decrease in said expression. In other preferred embodiments, the determined change in expression is a change in transcription of said one or more polynucleotides or a change in activity of a polypeptide, or expression product, encoded by said polynucleotide, including a change in the amount of said polypeptide synthesized, such as by a cell. The term "expression product" means that polypeptide or protein that is the natural translation product of the gene and any nucleic acid sequence coding equivalents resulting from genetic code degeneracy and thus coding for the same amino acid(s).

In additional preferred embodiments, said one or more polynucleotides are present in a cell, preferably a cancer cell, more preferably a colon cancer cell, and most preferably where the colon cancer cell is an adenocarcinoma cancer cell. In another preferred embodiment of the invention, the cell is a recombinant cell engineered to contain said set of genes.

Such methods serve to identify other compounds that have like activity, including expected therapeutic activity, as the compounds of the invention and thus serve as the basis for large scale screening assays for therapeutic compounds. As a result, one or more compounds of the invention can be utilized to determine the presents of gene sets and subsets within the genome of a cell. Thus, the set of all genes modulated by a group of structurally related compounds of the invention can form a gene set while the different sets of genes regulated by each compound of a group will form a subset. By way of non-limiting example, where a structurally related group of 5 of the compounds of the invention (all having generally the structure of Formula I) modulate (by increasing or decreasing) expression of determined genes 1–20, this latter group of genes forms a gene set. Further examination then determines that genes 1–6 are modulated by compound A, genes 7–10 are modulated by compound B, genes 2–4 and 9–12 are modulated by compound C, genes 10–20 are modulated by compound D and the even numbered genes are modulated by compound E. Each of these groups of genes, such as the genes modulated by compound C, is considered a subset of the gene set of genes 1–20. In an analogous manner, the genes modulated by compound E can be themselves further subdivided into at least 2 subsets wherein one subset is made up of the genes whose expression is increased by compound E while the other subset is made up of genes whose expression is decreased by compound E, thus yielding subsets of subsets. It should be noted that within the context of the present invention, it is not necessary to identify subsets and that each so-called subset is, in its own right, a gene set as used in the invention. The identification of sets and subsets is thus a function of the extent that a user of the methods of the invention wishes to determine modulation of genes resulting from contacting of one or more compounds of the invention. Thus, the genes modulated by a single compound form a gene set and it is not necessary, in carrying out the methods of the invention, to compare different groups of genes for modulation by more than one compound but this may, of course, be done.

In accordance with the foregoing, the present invention relates to a set of genes comprising a plurality of subsets of genes wherein each subset of said plurality is a gene set identified by the methods of the invention. The present invention also relates to compounds identified as having activity using the methods of the invention, such as novel compounds not specifically described herein by structure but which have been identified by their ability to modulates one or more gene sets modulated by compounds of the invention.

One example of a gene set according to the present invention comprises genes listed in Table 1, wherein the gene identifier is a GenBank accession number.

TABLE 1

| Direction | p value | Gene Identifier | Gene Name |
|---|---|---|---|
| Down | 9.73E−07 | NM_001827 | CDC28 protein kinase regulatory subunit 2 |
| Down | 1.09E−06 | NM_005375 | v-myb myeloblastosis viral oncogene homolog (avian) |
| Down | 2.78E−06 | NM_001568 | eukaryotic translation initiation factor 3, subunit 6 48 kDa |
| Down | 1.44E−05 | XM_071453 | YWHAE |
| Down | 2.41E−05 | XM_001668 | PDZK1 |
| Down | 2.74E−05 | NM_004336 | BUB1 budding uninhibited by benzimidazoles 1 homolog (yeast) |
| Down | 2.78E−05 | XM_007245 | YY1 |
| Down | 4.58E−05 | XM_056165 | YWHAH |
| Down | 0.000127924 | NM_003467 | chemokine (C-X-C motif) receptor 4 |
| Down | 0.00760276 | NM_006570 | Ras-related GTP-binding protein |
| Down | | NM_003600 | STK6 |
| Up | 9.17E−05 | NM_002087 | granulin |
| Up | 0.000145849 | NM_019113 | fibroblast growth factor 21 |
| Up | 0.000764702 | NM_002357 | MAX dimerization protein 1 |

The present invention also comprises methods for the preparation of compounds of formula I, and the relative key intermediates The compounds disclosed herein can be used to identify sets of genes related to a disease state such that all the members of the gene set are modulated by one or more of the compounds of the invention. Thus, the present invention further relates to a gene set wherein expression of each member of said gene set is modulated as a result of contacting said gene set with a compound of the invention. In particular embodiments thereof, expression of each member of said gene set is increased or is decreased as a result of said contacting. A preferred embodiment is where the gene set of the invention is present in a cell. Thus, a single gene set may be modulated by one or more of the compounds of the invention while a single compound may modulate one or more of said gene sets. Within a single gene set may be 2, 3, 5, 10 or more genes, some of which are increased in expression by a particular compound of the invention while the other members of the gene set are decreased by said contact.

Such gene sets can also be used as subsets to build a much larger set whose functioning is related in a general manner to a disease condition such that an increase or decrease in said expression is indicative of the disease state, such as where this disease state is cancer. In accordance therewith, the present invention contemplates a set of genes comprising a plurality of subsets of genes wherein each subset of said plurality is a gene set identified by the method of the invention.

Such gene sets find use in identifying and/or screening for other compounds having the same modulating ability. In accordance therewith, the present invention includes a method for identifying a test compound that modulates the expression of a gene set of the invention, comprising:

(a) contacting a test compound with one or more polynucleotides corresponding to each of the members of the gene set under conditions wherein the members of said gene set are being expressed;

(b) determining a change in expression of each of said one or more polynucleotides of step (a) as a result of said contacting;

wherein said change in expression of step (b) indicates modulation of the members of said gene set thereby identifying a test compound that modulates the expression of said gene set.

In a preferred embodiment of such method, the determined change in expression is a decrease in expression of said one or more polynucleotides.

In one preferred embodiment, the determined change in expression is a change in transcription of said one or more polynucleotides. In another preferred embodiment of such method, the change in expression is determined by determining a change in activity of a polypeptide encoded by said polynucleotide.

In accordance with the invention, the one or more polynucleotides used in such methods are present in a cell, preferably a cancer cell, most preferably a colon cancer cell, including an adenocarcinoma cancer cell.

In one such preferred embodiment, the cell is a recombinant cell, especially one engineered to contain gene set, such as by genetic engineering.

The present invention also relates to compounds found to have such activity with such gene sets including, but not limited to, compounds having the structure of:

3-Benzyloxy-1-methyl-1H-pyrrole-2,4-dicarboxylic acid 2-[(1-benzyl-piperidin-4-yl)-amide]4-hydroxyamide 3-Benzyloxy-1-methyl-1H-pyrrole-2,4-dicarboxylic acid 2-(4-dimethylamino-benzylamide)4-hydroxyamide 3-Benzyloxy-1-methyl-1H-pyrrole-2,4-dicarboxylic acid 2-[(3-dimethylamino-2,2-dimethyl-propyl)-amide]4-hydroxyamide 3-(4-Methoxy-benzyloxy)-1-methyl-1H-pyrrole-2,4-dicarboxylic acid 2-(4-dimethylaminobenzylamide)4-hydroxyamide 3-(4-Methoxy-benzyloxy)-1-methyl-1H-pyrrole-2,4-dicarboxylic acid 2-[(1-benzyl-piperidin-4-yl)-amide]4-hydroxyamide 3-(3,4-Dichloro-benzyloxy)-1-methyl-1H-pyrrole-2,4-dicarboxylic acid 2-(4-dimethylamino-benzylamide)4-hydroxyamide 3-(3,4-Dichloro-benzyloxy)-1-methyl-1H-pyrrole-2,4-dicarboxylic acid 4-hydroxyamide 2-{[3-(2-methyl-piperidin-1-yl)-propyl]-amide}

3-(3,4-Dichloro-benzyloxy)-1-methyl-1H-pyrrole-2,4-dicarboxylic acid 4-hydroxyamide 2-[(3-morpholin-4-yl-propyl)-amide]

3-(3,4-Dichloro-benzyloxy)-1-methyl-1H-pyrrole-2,4-dicarboxylic acid 2-[(3-dimethylamino-propyl)-amide]4-hydroxyamide 3-(3,4-Dichloro-benzyloxy)-1-methyl-1H-pyrrole-2,4-dicarboxylic acid 2-[(3-dimethylamino-2,2-dimethyl-propyl)-amide]4-hydroxyamide 3-(3,4-Dichloro-benzyloxy)-1-methyl-1H-pyrrole-2,4-dicarboxylic acid 4-hydroxyamide 2-{[2-(1-methyl-pyrrolidin-2-yl)-ethyl]-amide}

3-(3,4-Dichloro-benzyloxy)-1-methyl-1H-pyrrole-2,4-dicarboxylic acid 4-hydroxyamide 2-[(3-piperidin-1-yl-propyl)-amide]

3-(3,4-Dichloro-benzyloxy)-1-methyl-1H-pyrrole-2,4-dicarboxylic acid 2-[(3-diethylamino-propyl)-amide]4-hydroxyamide 3-(3,4-Dichloro-benzyloxy)-1-methyl-1H-pyrrole-2,4-dicarboxylic acid 2-[(3-dibutylamino-propyl)-amide]4-hydroxyamide 3-(3,4-Dichloro-benzyloxy)-1-methyl-1H-pyrrole-2,4-dicarboxylic acid 2-(4-amino-benzylamide)4-hydoxyamide 3-(3,4-Dichloro-benzyloxy)-1-methyl-1H-pyrrole-2,4-dicarboxylic acid 2-[(2-diethylamino-ethyl)-amide]4-hydroxyamide 3-(3,4-Dichloro-benzyloxy)-1-methyl-1H-pyrrole-2,4-dicarboxylic acid 2-[(1-benzyl-piperidin-4-yl)-amide]4-hydroxyamide 3-(3,4-Dichloro-benzyloxy)-1-methyl-1H-pyrrole-2,4-dicarboxylic acid 4-hydroxyamide 2-{[3-(4-methyl-piperazin-1-yl)-propyl]-amide}

3-(3,4-Dichloro-benzyloxy)-1-methyl-1H-pyrrole-2,4-dicarboxylic acid 2-[(3-azepan-1-yl-propyl)-amide]4-hydroxyamide 3-(3,4-Dichloro-benzyloxy)-1-methyl-1H-pyrrole-2,4-dicarboxylic acid 2-(4-aminomethyl-benzylamide)4-hydroxyamide 3-(3,4-Dichloro-benzyloxy)-1-methyl-1H-pyrrole-2,4-dicarboxylic acid 4-hydroxyamide 2-[(pyrrolidin-2-ylmethyl)-amide]

3-(3,4-Dichloro-benzyloxy)-1-methyl-1H-pyrrole-2,4-dicarboxylic acid 4-hydroxyamide 2-[(2-piperazin-1-yl-ethyl)-amide]

6-{[3-(3,4-Dichloro-benzyloxy)-4-hydroxycarbamoyl-1-methyl-1H-pyrrole-2-carbonyl]-amino}-hexanoic acid methyl ester 3-(3,4-Dichloro-benzyloxy)-1-methyl-1H-pyrrole-2,4-dicarboxylic acid 2-(3,4-dihydroxy-benzylamide)4-hydroxyamide 3-(3,4-Dichloro-benzyloxy)-1-methyl-1H-pyrrole-2,4-dicarboxylic acid 2-[(1-aza-bicyclo[2.2.2]oct-3-yl)-amide] 4-hydroxyamide 3-(3,4-Dichloro-benzyloxy)-4-hydroxycarbamoyl-1-methyl-1H-pyrrole-2-carboxylic acid 1-benzyl-piperidin-4-yl ester 5-(5-Benzyl-2,5-diaza-bicyclo[2.2.1]heptane-2-carbonyl)-4-(3,4-dichloro-benzyloxy)-1-methyl-1H-pyrrole-3-carboxylic acid hydroxyamide 3-(3,4-Dichloro-benzyloxy)-1-methyl-1H-pyrrole-2,4-dicarboxylic acid 4-hydroxyamide 2-{[4-(2-hydroxy-ethyl)-piperazin-1-yl]-amide}

5-([1,4']Bipiperidinyl-1'-carbonyl)-4-(3,4-dichloro-benzyloxy)-1-methyl-1H-pyrrole-3-carboxylic acid hydroxyamide 3-(3,4-Dichloro-benzyloxy)-1-methyl-1H-pyrrole-2,4-dicarboxylic acid 4-hydroxyamide 2-[(1-naphthalen-1-yl-ethyl)-amide]

3-(3,4-Dichloro-benzyloxy)-1-methyl-1H-pyrrole-2,4-dicarboxylic acid 2-[(benzo[1,3]dioxol-5-ylmethyl)-amide] 4-hydroxyamide 3-(3,4-Dichloro-benzyloxy)-1-methyl-1H-pyrrole-2,4-dicarboxylic acid 4-hydroxyamide 2-{[(4-methyl-pyridin-2-yl)-phenyl-methyl]-amide}

5-(N'-Benzyl-hydrazinocarbonyl)-4-(3,4-dichloro-benzyloxy)-1-methyl-1H-pyrrole-3-carboxylic acid hydroxyamide 3-(3,4-Dichloro-benzyloxy)-1-methyl-1H-pyrrole-2,4-dicarboxylic acid 2-{[2-(1-benzyl-piperidin-4-ylamino)-phenyl]-amide}4-hydroxyamide 3-(3,4-Dichloro-benzyloxy)-1-methyl-1H-pyrrole-2,4-dicarboxylic acid 4-hydroxyamide 2{[4-(4-methyl-piperidin-1-yl)-phenyl]-amide}

3-(3,4-Dichloro-benzyloxy)-1-methyl-1H-pyrrole-2,4-dicarboxylic acid 4-hydroxyamide 2-piperidin-4-ylamide 5-(4-Amino-piperidine-1-carbonyl)-4-(3,4-dichloro-benzyloxy)-1-methyl-1H-pyrrole-3-carboxylic acid hydroxyamide 3-(3,4-Dichloro-benzyloxy)-1-methyl-1H-pyrrole-2,4-dicarboxylic acid 2-{[1-(4-dimethylamino-butyryl)-piperidin-4-yl]-amide}4-hydroxyamide 3-(3,4-Dichloro-benzyloxy)-1-methyl-1H-pyrrole-2,4-dicarboxylic acid 2-{[1-(4-cyano-benzyl)-piperidin-4-yl]-amide}4-hydroxyamide 3-(3,4-Dichloro-benzyloxy)-1-methyl-1H-pyrrole-2,4-dicarboxylic acid 4-hydroxyamide 2-[(4-methyl-piperazin-1-yl)-amide]

3-(3,4-Dichloro-benzyloxy)-1-methyl-1H-pyrrole-2,4-dicarboxylic acid 4-hydroxyamide 4-[(1,2,2,6,6-pentamethyl-piperidin-4-yl)-amide]

4-{[3-(3,4-Dichloro-benzyloxy)-4-hydroxycarbamoyl-1-methyl-1H-pyrrole-2-carbonyl]-amino}-piperidine-1-carboxylic acid ethyl ester 3-(3,4-Dichloro-benzyloxy)-1-methyl-1H-pyrrole-2,4-dicarboxylic acid 4-hydroxyamide 2-indan-1-ylamide 3-(3,4-Dichloro-benzyloxy)-1-methyl-1H-pyrrole-2,4-dicarboxylic acid 2-[(9H-fluoren-9-yl)-amide]4-hydroxyamide 3-(3,4-Dichloro-benzyloxy)-1-methyl-1H-pyrrole-2,4-dicarboxylic acid 4-hydroxyamide 2-[(1,2,3,4-tetrahydronaphthalen-1-yl)-amide]

3-(3,4-Dichloro-benzyloxy)-1-methyl-1H-pyrrole-2,4-dicarboxylic acid 2-[(4-benzyl-morpholin-2-ylmethyl)-amide]4-hydroxyamide 3-(3,4-Dichloro-benzyloxy)-1-methyl-1H-pyrrole-2,4-dicarboxylic acid 2-{[2-(4-benzyl-piperazin-1-yl)-ethyl]-amide}4-hydroxyamide 3-(3,4-Dichloro-benzyloxy)-1-methyl-1H-pyrrole-2,4-dicarboxylic acid 2-[(1-benzyl-piperidin-3-yl)-amide]4-hydroxyamide 5-(4-Benzyl-piperazine-1-carbonyl)-4-(3,4-dichloro-benzyloxy)-1-methyl-1H-pyrrole-3-carboxylic acid hydroxyamide 3-(3,4-Dichloro-benzyloxy)-1-methyl-1H-pyrrole-2,4-dicarboxylic acid 2-[(2,3-dihydro-benzo[1,4]dioxin-2-ylmethyl)-amide]4-hydroxyamide 3-(3,4-Dichloro-benzyloxy)-1-methyl-1H-pyrrole-2,4-dicarboxylic acid 4-({3-[4-(2-chloro-6-fluoro-benzyl)-piperazin-1-yl]-propyl}amide)4-hydroxyamide 3-(3,4-Dichloro-benzyloxy)-1-methyl-1H-pyrrole-2,4-dicarboxylic acid 2-piperidin-1-ylamide 3-(3,4-Dichloro-benzyloxy)-1-methyl-1H-pyrrole-2,4-dicarboxylic acid 4-hydroxyamide 2-[(2-hydroxy-indan-1-yl)-amide]

3-(3,4-Dichloro-benzyloxy)-1-methyl-1H-pyrrole-2,4-dicarboxylic acid 2-[(1-benzyl-pyrrolidin-3-yl)-amide]4-hydroxyamide 3-(3,4-Dichloro-benzyloxy)-1-methyl-1H-pyrrole-2,4-dicarboxylic acid 4-hydroxyamide 2-morpholin-4-ylamide 3-(3,4-Dichloro-benzyloxy)-1-methyl-1H-pyrrole-2,4-dicarboxylic acid 2-azepan-1-ylamide 4-hydroxyamide 3-(3,4-Dichloro-benzyloxy)-1-methyl-1H-pyrrole-2,4-dicarboxylic acid 4-hydroxyamide 2-[(8-methyl-8-aza-bicyclo[3.2.1]oct-3-yl)-amide]

3-(3,4-Dichloro-benzyloxy)-1-methyl-1H-pyrrole-2,4-dicarboxylic acid 4-hydroxyamide 2-[(2-hydroxy-indan-1-yl)-amide]

3-(3,4-Dichloro-benzyloxy)-1-methyl-1H-pyrrole-2,4-dicarboxylic acid 4-hydroxyamide 2-[(2-methoxymethyl-pyrrolidin-1-yl)-amide]

3-(3,4-Dichloro-benzyloxy)-1-methyl-1H-pyrrole-2,4-dicarboxylic acid 2-[(2-carbamoyl-cyclohexyl)-amide]4-hydroxyamide 3-(3,4-Dichloro-benzyloxy)-1-methyl-1H-pyrrole-2,4-dicarboxylic acid 2-({3-[4-(3-amino-propyl)-piperazin-1-yl]-propyl}-amide)4-hydroxyamide 5-(4-Benzhydryl-piperazine-1-carbonyl)-4-(3,4-dichloro-benzyloxy)-1-methyl-1H-pyrrole-3-carboxylic acid hydroxyamide 4-(3,4-Dichloro-benzyloxy)-5-[4-(4-fluoro-benzyl)-[1,4]diazepane-1-carbonyl]-1-methyl-1H-pyrrole-3-carboxylic acid hydroxyamide 4-(3,4-Dichloro-benzyloxy)-5-{4-[2-(2,5-dimethyl-pyrrol-1-yl)-ethyl]-piperazine-1-carbonyl}-1-methyl-1H-pyrrole-3-carboxylic acid hydroxyamide 3-(3,4-Dichloro-benzyloxy)-1-methyl-1H-pyrrole-2,4-dicarboxylic acid 4-hydroxyamide 2-(4-pyrazol-1-yl-benzylamide)

4-(3,4-Dichloro-benzyloxy)-1-methyl-5-[4-(2-methyl-quinolin-4-yl)-piperazine-1-carbonyl]-1H-pyrrole-3-carboxylic acid hydroxyamide 3-(3,4-Dichloro-benzyloxy)-1-methyl-1H-pyrrole-2,4-dicarboxylic acid 2-benzylamide 4-hydroxyamide 3-(3,4-Dichloro-benzyloxy)-1-methyl-1H-pyrrole-2,4-dicarboxylic acid 4-hydroxyamide 2-(2-methoxy-benzylamide)

3-(3,4-Dichloro-benzyloxy)-1-methyl-1H-pyrrole-2,4-dicarboxylic acid 4-hydroxyamide 2-(3-methoxy-benzylamide)

3-(3,4-Dichloro-benzyloxy)-1-methyl-1H-pyrrole-2,4-dicarboxylic acid 2-(2,4-dimethoxy-benzylamide)4-hydroxyamide 3-(3,4-Dichloro-benzyloxy)-1-methyl-1H-pyrrole-2,4-dicarboxylic acid 2-(3,4-dimethoxy-benzylamide)4-hydroxyamide 3-(3,4-Dichloro-benzyloxy)-1-methyl-1H-pyrrole-2,4-dicarboxylic acid 4-hydroxyamide 4-(2,4,6-trimethoxy-benzylamide)

5-(4-Benzo[1,3]dioxol-5-ylmethyl-piperazine-1-carbonyl)-4-(3,4-dichloro-benzyloxy)-1-methyl-1H-pyrrole-3-carboxylic acid hydroxyamide 3-(3,4-Dichloro-benzyloxy)-1-methyl-1H-pyrrole-2,4-dicarboxylic acid 4-hydroxyamide 2-{[2-(4-hydroxy-phenyl)-ethyl]-amide}

3-(3,4-Dichloro-benzyloxy)-1-methyl-1H-pyrrole-2,4-dicarboxylic acid 4-hydroxyamide 2-[(pyridin-3-ylmethyl)-amide]

3-(3,4-Dichloro-benzyloxy)-1-methyl-1H-pyrrole-2,4-dicarboxylic acid 4-hydroxyamide 2-[(pyridin-4-ylmethyl)-amide]

3-(3,4-Dichloro-benzyloxy)-1-methyl-1H-pyrrole-2,4-dicarboxylic acid 4-hydroxyamide 2-[(pyridin-2-ylmethyl)-amide]

3-(3,4-Dichloro-benzyloxy)-1-methyl-1H-pyrrole-2,4-dicarboxylic acid 4-hydroxyamide 2-(4-pentyl-benzylamide)

3-(3,4-Dichloro-benzyloxy)-1-methyl-1H-pyrrole-2,4-dicarboxylic acid 4-{[2-(2-chloro-6-fluoro-benzylsulfanyl)-ethyl]-amide}4-hydroxyamide 3-(3,4-Dichloro-benzyloxy)-1-methyl-1H-pyrrole-2,4-dicarboxylic acid 4-{[2-(2,6-dichloro-benzylsulfanyl)-ethyl]-amide}4-hydroxyamide 3-(3,4-Dichloro-benzyloxy)-1-methyl-1H-pyrrole-2,4-dicarboxylic acid 2-{[3-(3-acetylamino-phenoxy)-propyl]-amide}4-hydroxyamide 3-(3,4-Dichloro-benzyloxy)-1-methyl-1H-pyrrole-2,4-dicarboxylic acid 4-hydroxyamide 2-[(1-methyl-1H-pyrrol-2-ylmethyl)-amide]

3-(3,4-Dichloro-benzyloxy)-1-methyl-1H-pyrrole-2,4-dicarboxylic acid 4-hydroxyamide 2-[(2-phenyl-thiazol-4-ylmethyl)-amide]

3-(3,4-Dichloro-benzyloxy)-1-methyl-1H-pyrrole-2,4-dicarboxylic acid 2-{[2-(5-dimethylaminomethyl-furan-2-ylmethylsulfanyl)-ethyl]-amide}4-hydroxyamide 4-({[3-(3,4-Dichloro-benzyloxy)4-hydroxycarbamoyl-1-methyl-1H-pyrrole-2-carbonyl]-amino}-methyl)-benzoic acid methyl ester 3-(3,4-Dichloro-benzyloxy)-1-methyl-1H-pyrrole-2,4-dicarboxylic acid 4-hydroxyamide 2-(4-methyl-benzylamide)

3-(3,4-Dichloro-benzyloxy)-1-methyl-1H-pyrrole-2,4-dicarboxylic acid 4-hydroxyamide 2-{[2-(2-trifluoromethyl-quinolin-4-ylsulfanyl)-ethyl]-amide}

3-(3,4-Dichloro-benzyloxy)-1-methyl-1H-pyrrole-2,4-dicarboxylic acid 4-hydroxyamide 2-(3-pyrrol-1-yl-benzylamide)

3-(3,4-Dichloro-benzyloxy)-1-methyl-1H-pyrrole-2,4-dicarboxylic acid 4-hydroxyamide 2-(4-[1,2,3]thiadiazol-4-yl-benzylamide)

3-(3,4-Dichloro-benzyloxy)-1-methyl-1H-pyrrole-2,4-dicarboxylic acid 4-hydroxyamide 2-(4-thiophen-3-yl-benzylamide)

3-(3,4-Dichloro-benzyloxy)-1-methyl-1H-pyrrole-2,4-dicarboxylic acid 2-[(2,3-dihydro-benzo[1,4]dioxin-6-ylmethyl)-amide]4-hydroxyamide 3-(3,4-Dichloro-benzyloxy)-1-methyl-1H-pyrrole-2,4-dicarboxylic acid 4-(2-chloro-6-phenoxy-benzylamide)4-hydroxyamide 3-(2,4-Dichloro-benzyloxy)-1-methyl-1H-pyrrole-2,4-dicarboxylic acid 2-(4-dimethylamino-benzylamide)4-hydroxyamide 3-(2,6-Dichloro-benzyloxy)-1-methyl-1H-pyrrole-2,4-dicarboxylic acid 2-(4-dimethylamino-benzylamide)4-hydroxyamide 1-Benzyl-3-(3,4-dichloro-benzyloxy)-1H-pyrrole-2,4-dicarboxylic acid 2-[(1-benzyl-piperidin-4-yl)-amide]4-hydroxyamide 1-Benzyl-3-(3,4-dichloro-benzyloxy)-1H-pyrrole-2,4-dicarboxylic acid 2-[(1-benzyl-piperidin-3-yl)-amide]4-hydroxyamide 1-Benzyl-3-(3,4-dichloro-benzyloxy)-1H-pyrrole-2,4-dicarboxylic acid 2-{[2-(1-benzyl-piperidin-4-ylamino)-phenyl]-amide}4-hydroxyamide 3-Benzyloxy-1-methyl-1H-pyrrole-2,4-dicarboxylic acid 4-[(1-benzyl-piperidin-4-yl)-amide]2-hydroxyamide 3-Benzyloxy-1-methyl-1H-pyrrole-2,4-dicarboxylic acid 2-hydroxyamide 4-{[3-(4-methyl-piperazin-1-yl)-propyl]-amide}

3-(4-Methoxy-benzyloxy)-1-methyl-1H-pyrrole-2,4-dicarboxylic acid 4-[(1-benzyl-piperidin-4-yl)-amide]2-hydroxyamide 3-(3,4-Dichloro-benzyloxy)-1-methyl-1H-pyrrole-2,4-dicarboxylic acid 4-(4-dimethylamino-benzylamide)2-hydroxyamide 3-(3,4-Dichloro-benzyloxy)-1-methyl-1H-pyrrole-2,4-dicarboxylic acid 4-[(1-benzyl-piperidin-4-yl)-amide]2-hydroxyamide 4-(4-Benzyl-piperazine-1-carbonyl)-3-(3,4-dichloro-benzyloxy)-1-methyl-1H-pyrrole-2-carboxylic acid hydroxyamide 3-(3,4-Dichloro-benzyloxy)-1-methyl-1H-pyrrole-2,4-dicarboxylic acid 4-[(1-benzyl-piperidin-3-yl)-amide]2-hydroxyamide 3-(3,4-Dichloro-benzyloxy)-1-methyl-1H-pyrrole-2,4-dicarboxylic acid 4-[(1-benzyl-pyrrolidin-3-yl)-amide]2-hydroxyamide 3-(2,6-Dichloro-benzyloxy)-1-methyl-1H-pyrrole-2,4-dicarboxylic acid 4-[(1-benzyl-piperidin-4-yl)-amide]2-hydroxyamide 4-(4-Benzyl-piperazine-1-carbonyl)-3-(2,6-dichloro-benzyloxy)-1-methyl-1H-pyrrole-2-carboxylic acid hydroxyamide 3-(2,6-Dichloro-benzyloxy)-1-methyl-1H-pyrrole-2,4-dicarboxylic acid 4-[(1-benzyl-piperidin-3-yl)-amide]2-hydroxyamide 3-(2,6-Dichloro-benzyloxy)-1-methyl-1H-pyrrole-2,4-dicarboxylic acid 4-[(1-benzyl-pyrrolidin-3-yl)-amide]2-hydroxyamide 3-(4-Cyano-benzyloxy)-1-methyl-1H-pyrrole-2,4-dicarboxylic acid 4-[(1-benzyl-piperidin-3-yl)-amide]2-hydroxyamide 3-(4-Cyano-benzyloxy)-1-methyl-1H-pyrrole-2,4-dicarboxylic acid 4-[(1-benzyl-piperidin-4-yl)-amide]2-hydroxyamide 4-(4-Benzyl-piperazine-1-carbonyl)-3-(4-cyano-benzyloxy)-1-methyl-1H-pyrrole-2-carboxylic acid hydroxyamide 3-(4-Cyano-benzyloxy)-1-methyl-1H-pyrrole-2,4-dicarboxylic acid 4-[(1-benzyl-pyrrolidin-3-yl)-amide]2-hydroxyamide 1-Methyl-3-(pyridin-4-ylmethoxy)-1H-pyrrole-2,4-dicarboxylic acid 4-[(1-benzyl-pyrrolidin-3-yl)-amide]2-hydroxyamide 4-(4-Benzyl-piperazine-1-carbonyl)-1-methyl-3-(pyridin-4-ylmethoxy)-1H-pyrrole-2-carboxylic acid hydroxyamide 1-Methyl-3-(pyridin-4-ylmethoxy)-1H-pyrrole-2,4-dicarboxylic acid 4-[(1-benzyl-piperidin-4-yl)-amide]2-hydroxyamide 1-Methyl-3-(pyridin-4-ylmethoxy)-1H-pyrrole-2,4-dicarboxylic acid 4-[(1-benzyl-piperidin-3-yl)-amide]2-hydroxyamide, or 3-(3,4-Difluoro-benzyloxy)-1-methyl-1H-pyrrole-2,4-dicarboxylic acid 4-[(1-benzyl-piperidin-4-yl)-amide]2-hydroxyamide.

COMPOUND PREPARATION

By methods provided herein, and by obvious modification thereto, the compounds of this invention may be prepared from the appropriate starting materials. The exemplified compounds, and the methods of their preparation, are presented merely by way of example, and the presentation of selected examples is not intended to limit the scope of the invention.

In the most general embodiment the method of preparing the particularly preferred compounds of formula I is presented in Scheme 1. The starting materials (1) are known (Momose et al., *Chem. Pharm. Bull.* 26:2224–2232 (1978)). In the first step they are transformed into stable active esters (2) which allow for easy synthesis of amides 3 at room temperature.

This particular embodiment further comprises the conversion of the 3-hydroxyl group into alkyl, allyl or benzyl derivatives (4) by reaction with a suitable halide in acetone, DMF or other suitable solvent, in the presence of potassium carbonate. The time and temperature required for the reaction will vary, depending upon the nature of reagents. Generally, the reaction mixture will be gradually raised in temperature until a suitable reaction rate is obtained.

Scheme 1

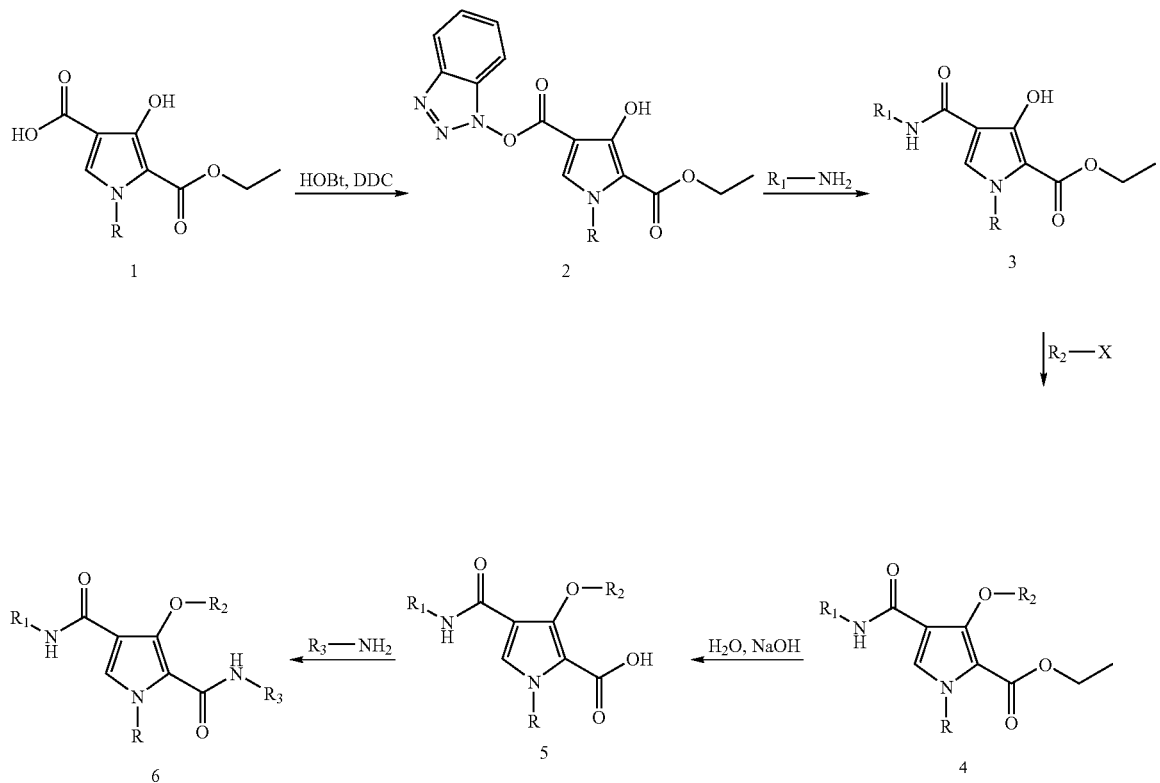

The protection of hydroxyl group allows for easy conversion of the ethyl ester 4 to carboxylic acid 5, by hydrolysis under basic conditions. In turn, acids 5 may be coupled with various amines using 1-[3-(dimethylamino)propyl]-3-ethylcarbodiimide hydrochloride or other coupling agents, to provide amide derivative 6. In the last step, hydroxamic acid moiety is formed by acidic deprotection.

Specific examples for making the compounds of the present invention are set forth and in Examples 1–124. These steps may be varied to increase yield of desired product. The skilled artisan will recognize that the judicious choice of reactants, solvents, and temperatures is an important component in any successful synthesis. Determination of optimal conditions, etc. is routine. Thus, the skilled artisan can make a variety of compounds using the guidance of the scheme above.

The skilled artisan will recognize that some reactions are best carried out when another potentially reactive functionality on the molecule is masked or protected, thus avoiding any undesirable side reactions and/or increasing the yield of the reaction. Often protecting groups are used to accomplish such increased yields or to avoid the undesired reactions. Such reactions are well within the ability of the skilled artisan. Some examples are found in T. Greene, *Protecting Groups in Organic Synthesis*.

In addition, it is to be appreciated that one optical isomer may have favorable properties over the other and thus the disclosure of a racemic mixture within the present invention may also include either optically active isomer if such isomer has advantageous physiological activity in accordance with the methods of the invention.

Commercial reagents are purchased from Aldrich Chemical Company (Milwaukee, Wis.). and used without further purification. Column chromatography is performed on 70–230-mesh silica gel (Aldrich). Melting points are determined on a Mettler capillary melting point apparatus and are uncorrected. $^1$H NMR spectra are recorded on a Bruker spectrometer operating at 400 MHz. Chemical shifts are reported as δ units in ppm downfield from internal trimethylsilane. NMR abbreviations used are as follows: br (broad), s (singlet), d (doublet), t (triplet), q (quartet), qu (quintet), m (multiplet). Coupling constants are given in Hz.

COMPOUND PREPARATION

By methods provided herein, and by obvious modification thereto, the compounds of this invention may be prepared from the appropriate starting materials. The exemplified compounds, and the methods of their preparation, are presented merely by way of example, and the presentation of selected examples is not intended to limit the scope of the invention.

Scheme 1

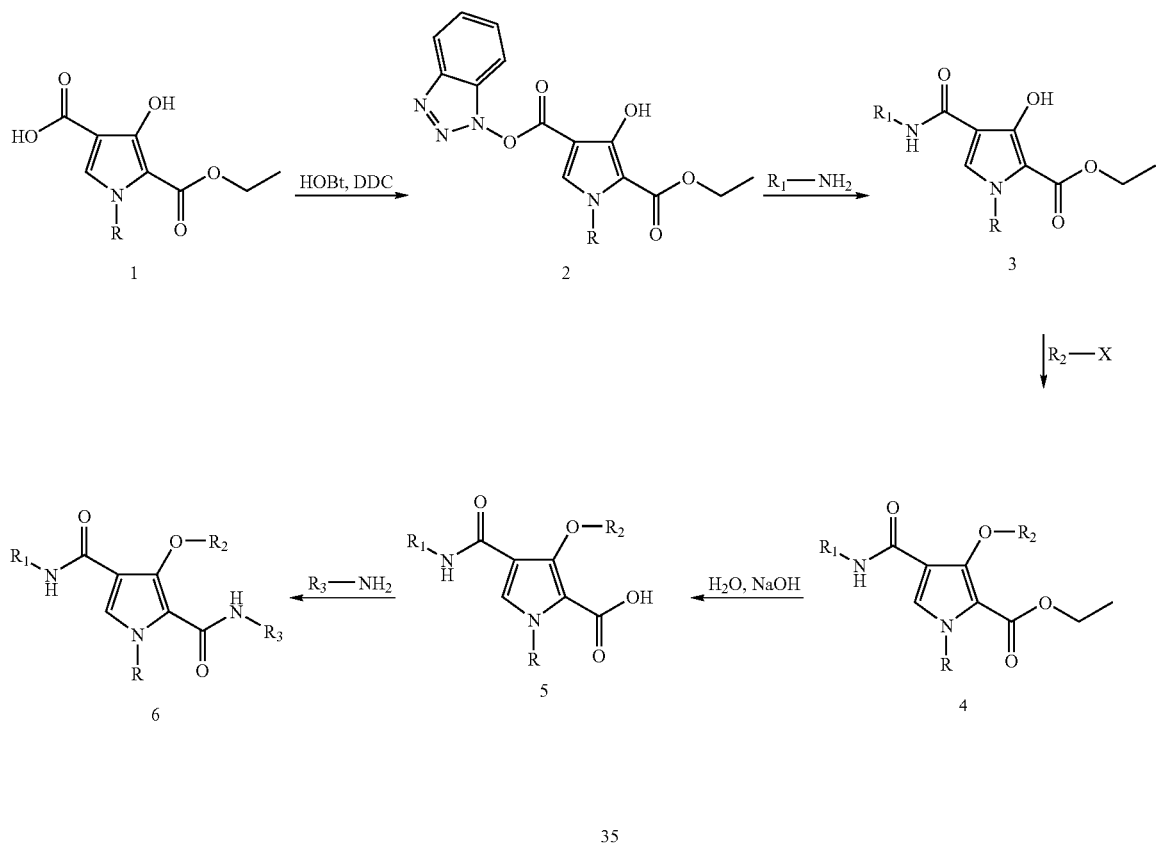

In the most general embodiment the method of preparing the particularly preferred compounds of formula I is presented in Scheme 1. The starting materials (1) are known (Momose et al., *Chem. Pharm. Bull.* 26:2224–2232 (1978)). In the first step they are transformed into stable active esters (2) which allow for easy synthesis of amides 3 at room temperature.

This particular embodiment further comprises the conversion of the 3-hydroxyl group into alkyl, allyl or benzyl derivatives (4) by reaction with a suitable halide in acetone, DMF or other suitable solvent, in the presence of potassium carbonate. The time and temperature required for the reaction will vary, depending upon the nature of reagents. Generally, the reaction mixture will be gradually raised in temperature until a suitable reaction rate is obtained.

The protection of hydroxyl group allows for easy conversion of the ethyl esters 4 to carboxylic acids 5, by hydrolysis under basic conditions. In turn, acids 5 may be coupled with various amines using 1-[3-(dimethylamino)propyl]-3-ethylcarbodiimide hydrochloride or other coupling agents, to provide amide derivatives 6. In the last step, hydroxamic acid moiety is formed by acidic deprotection.

Specific examples for making the compounds of the present invention are set forth and in Examples 1–124. These steps may be varied to increase yield of desired product. The skilled artisan will recognize the judicious choice of reactants, solvents, and temperatures is an important component in any successful synthesis. Determination of optimal conditions, etc. is routine. Thus, the skilled artisan can make a variety of compounds using the guidance of the scheme above.

The skilled artisan will recognize that some reactions are best carried out when another potentially reactive functionality on the molecule is masked or protected, thus avoiding any undesirable side reactions and/or increasing the yield of the reaction. Often the skilled artisan utilizes protecting groups to accomplish such increased yields or to avoid the undesired reactions. Such reactions are well within the ability of the skilled artisan. Some examples are found in T. Greene, *Protecting Groups in Organic Synthesis*.

In addition, it is to be appreciated that one optical isomer may have favorable properties over the other and thus the disclosure of a racemic mixture within the present invention may also include either optically active isomer if physiologically active in accordance with the methods of the invention.

Commercial reagents are purchased from Aldrich Chemical Company (Milwaukee, Wis.). and used without further purification. Column chromatography is performed on 70–230-mesh silica gel (Aldrich). Melting points are determined on an capillary melting point apparatus and are uncorrected. $^1$H NMR spectra are recorded on Bruker spectrometer operating at 400 MHz. Chemical shifts are reported as δ units in ppm downfield from internal trimethylsilane. NMR abbreviations used are as follows: br (broad), s (singlet), d (doublet), t (triplet), q (quartet), qu (quintet), m (multiplet). Coupling constants are given in Hz.

EXAMPLES 1–96
The following chart shows the structure of compounds made according to the description in Examples 1–24 described below:
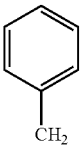
| Example | R1 | R2 | [M + H]⁺ |
|---|---|---|---|
| 1 | 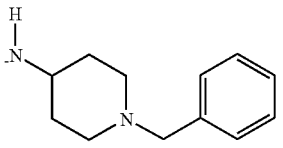 | 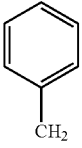 | 463 |
| 2 | 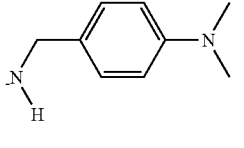 | 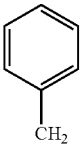 | 423 |
| 3 |  | 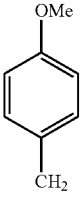 | 403 |
| 4 | 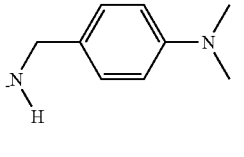 | 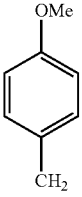 | 453 |
| 5 | 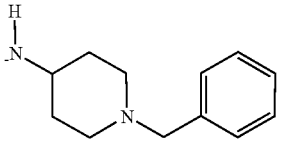 | 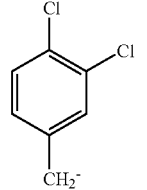 | 493 |
| 6 | 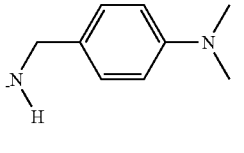 | | 491 |

-continued
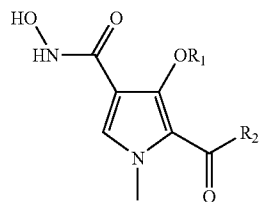
| Example | R1 | R2 | [M + H]+ |
|---|---|---|---|
| 7 | 3,4-dichlorobenzyl | -NH-(CH2)3-(2-methylpiperidin-1-yl) | 497 |
| 8 | 3,4-dichlorobenzyl | -NH-(CH2)3-piperidin-1-yl | 485 |
| 9 | 3,4-dichlorobenzyl | -N(CH3)-(CH2)3-N(CH3)2 | 457 |
| 10 | 3,4-dichlorobenzyl | -NH-CH2-C(CH3)2-CH2-N(CH3)2 | 485 |
| 11 | 3,4-dichlorobenzyl | -NH-(CH2)2-(1-methylpyrrolidin-2-yl) | 469 |
| 12 | 3,4-dichlorobenzyl | -NH-(CH2)3-piperidin-1-yl | 483 |

-continued
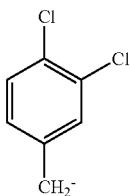
| Example | R1 | R2 | [M + H]⁺ |
|---|---|---|---|
| 13 | 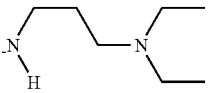 | 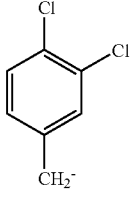 | 471 |
| 14 | 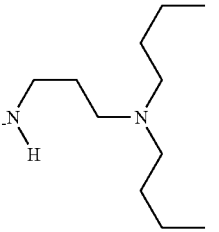 | 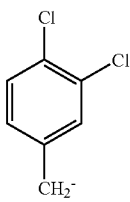 | 527 |
| 15 | 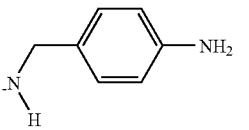 | 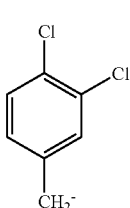 | 463 |
| 16 | 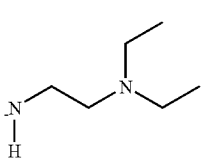 | 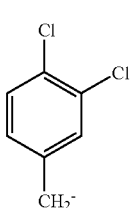 | 457 |
| 17 | 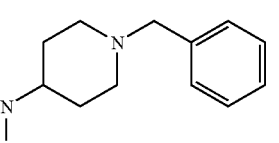 | 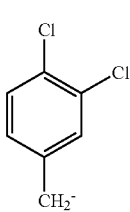 | 531 |
| 18 | 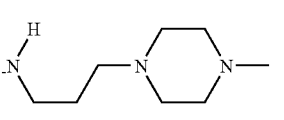 | | 497 |

-continued
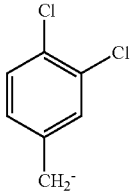
| Example | R1 | R2 | [M + H]+ |
|---|---|---|---|
| 19 | 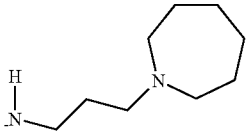 | 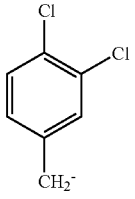 | 497 |
| 20 | 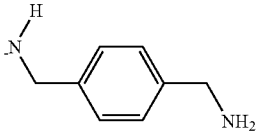 | 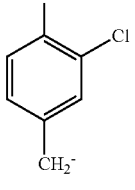 | 477 |
| 21 | 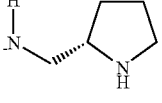 | 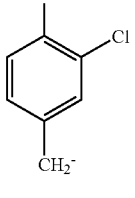 | 441 |
| 22 | 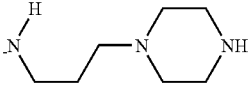 | 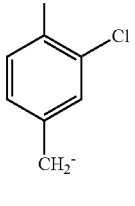 | 470 |
| 23 | 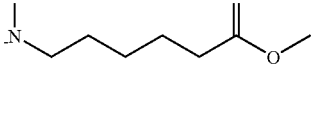 | 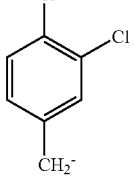 | 486 |
| 24 | 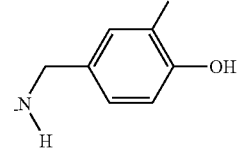 | | 480 |

-continued
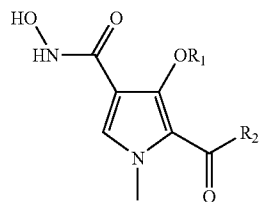
| Example | R1 | R2 | [M + H]+ |
|---|---|---|---|
| 25 | 3,4-dichlorobenzyl | 3-aminoquinuclidine | 481 |
| 26 | 3,4-dichlorobenzyl | 1-benzylpiperidin-4-yloxy | 532 |
| 27 | 3,4-dichlorobenzyl | 2-benzyl-2,5-diazabicyclo[2.2.1]heptane | 529 |
| 28 | 3,4-dichlorobenzyl | 4-(2-hydroxyethyl)piperazin-1-ylamino | 486 |
| 29 | 3,4-dichlorobenzyl | 4-piperidinopiperidin-1-yl | 509 |
| 30 | 3,4-dichlorobenzyl | 1-(1-naphthyl)ethylamino | 512 |

-continued

| Example | R1 | R2 | [M + H]+ |
|---|---|---|---|
| 31 | 3,4-dichlorobenzyl | benzo[1,3]dioxol-5-ylmethylamino | 492 |
| 32 | 3,4-dichlorobenzyl | (4-methylpyridin-2-yl)(phenyl)methylamino | 539 |
| 33 | 3,4-dichlorobenzyl | (3-hydroxy-1-phenylpropyl)amino | 492 |
| 34 | 3,4-dichlorobenzyl | N'-benzylhydrazino | 463 |
| 35 | 3,4-dichlorobenzyl | 2-[(1-benzylpiperidin-4-yl)amino]pyridin-3-ylamino | 622 |
| 36 | 3,4-dichlorobenzyl | 4-(4-methylpiperidin-1-yl)phenylamino | 531 |

-continued
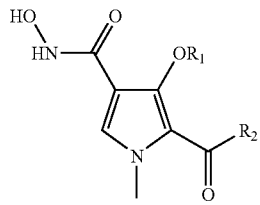
| Example | R1 | R2 | [M + H]+ |
|---|---|---|---|
| 37 | 3,4-dichlorobenzyl | 4-piperidinylamino (NH via 4-position, piperidine NH) | 441 |
| 38 | 3,4-dichlorobenzyl | 4-amino-piperidin-1-yl | 441 |
| 39 | 3,4-dichlorobenzyl | 1-(4-dimethylaminobutanoyl)piperidin-4-ylamino | 554 |
| 40 | 3,4-dichlorobenzyl | 1-(4-cyanobenzyl)piperidin-4-ylamino | 556 |
| 41 | 3,4-dichlorobenzyl | 4-methylpiperazin-1-ylamino | 466 |
| 42 | 3,4-dichlorobenzyl | 1,2,2,6,6-pentamethylpiperidin-4-ylamino | 511 |

-continued
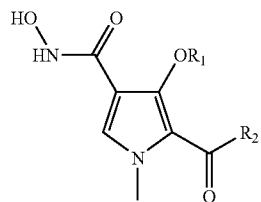
| Example | R1 | R2 | [M + H]⁺ |
|---|---|---|---|
| 43 | 3,4-dichlorobenzyl | ethyl 4-aminopiperidine-1-carboxylate | 513 |
| 44 | 3,4-dichlorobenzyl | 1-aminoindane | 474 |
| 45 | 3,4-dichlorobenzyl | 9-aminofluorene | 522 |
| 46 | 3,4-dichlorobenzyl | 1-amino-1,2,3,4-tetrahydronaphthalene | 488 |
| 47 | 3,4-dichlorobenzyl | (4-benzylmorpholin-2-yl)methylamine | 547 |
| 48 | 3,4-dichlorobenzyl | 2-(4-benzylpiperazin-1-yl)ethylamine | 560 |

-continued
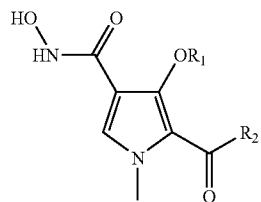
| Example | R1 | R2 | [M + H]+ |
|---|---|---|---|
| 49 | 3,4-dichlorobenzyl | (3R)-1-benzylpiperidin-3-ylamino | 531 |
| 50 | 3,4-dichlorobenzyl | 4-benzylpiperazin-1-yl | 517 |
| 51 | 3,4-dichlorobenzyl | (2,3-dihydro-1,4-benzodioxin-2-ylmethyl)amino | 506 |
| 52 | 3,4-dichlorobenzyl | 2-[4-(2-chloro-6-fluorobenzyl)piperazin-1-yl]ethylamino | 626 |
| 53 | 3,4-dichlorobenzyl | piperidin-1-ylamino | 441 |
| 54 | 3,4-dichlorobenzyl | (1S,2R)-2-hydroxyindan-1-ylamino | 490 |

-continued
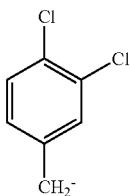
| Example | R1 | R2 | [M + H]+ |
|---|---|---|---|
| 55 | 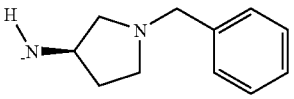 | 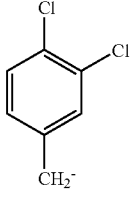 | 517 |
| 56 | 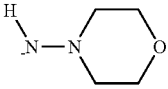 | 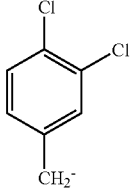 | 443 |
| 57 | 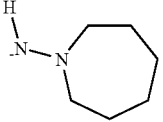 | 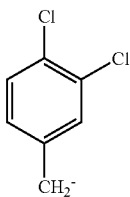 | 455 |
| 58 | 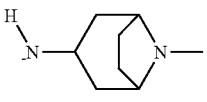 | 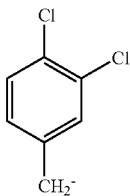 | 481 |
| 59 | 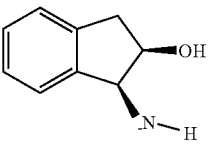 | 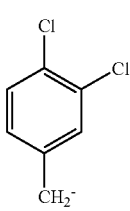 | 490 |
| 60 | 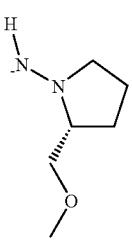 | | 471 |

-continued

| Example | R1 | R2 | [M + H]+ |
|---|---|---|---|
| 61 | 3,4-dichlorobenzyl (-CH2-C6H3(Cl)2) | (1S,2S)-2-aminocyclohexane-1-carboxamide | 483 |
| 62 | 3,4-dichlorobenzyl | 1-(3-aminopropyl)-4-(3-aminopropyl)piperazine (via one N) | 541 |
| 63 | 3,4-dichlorobenzyl | 4-benzhydrylpiperazin-1-yl | 593 |
| 64 | 3,4-dichlorobenzyl | 4-(4-fluorobenzyl)-1,4-diazepan-1-yl | 549 |
| 65 | 3,4-dichlorobenzyl | 4-[2-(2,5-dimethyl-1H-pyrrol-1-yl)ethyl]piperazin-1-yl | 548 |
| 66 | 3,4-dichlorobenzyl | [4-(1H-pyrazol-1-yl)benzyl]amino | 514 |

-continued
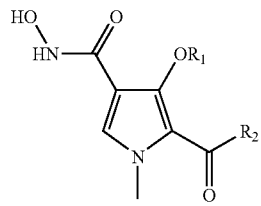
| Example | R1 | R2 | [M + H]+ |
|---|---|---|---|
| 67 | 3,4-dichlorobenzyl | 2-methyl-4-(piperazin-1-yl)quinoline (N-linked) | 568 |
| 68 | 3,4-dichlorobenzyl | benzylamino | 448 |
| 69 | 3,4-dichlorobenzyl | 2-methoxybenzylamino | 478 |
| 70 | 3,4-dichlorobenzyl | 3-methoxybenzylamino | 478 |
| 71 | 3,4-dichlorobenzyl | 2,4-dimethoxybenzylamino | 508 |
| 72 | 3,4-dichlorobenzyl | 3,4-dimethoxybenzylamino | 508 |

-continued
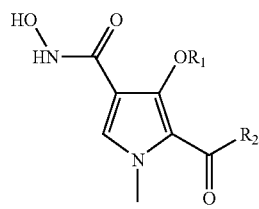
| Example | R1 | R2 | [M + H]+ |
|---|---|---|---|
| 73 | 3,4-dichlorobenzyl | (2,4,6-trimethoxybenzyl)amino | 538 |
| 74 | 3,4-dichlorobenzyl | 4-(1,3-benzodioxol-5-ylmethyl)piperazin-1-yl | 561 |
| 75 | 3,4-dichlorobenzyl | [2-(4-hydroxyphenyl)ethyl]amino | 478 |
| 76 | 3,4-dichlorobenzyl | (pyridin-3-ylmethyl)amino | 449 |
| 77 | 3,4-dichlorobenzyl | (pyridin-4-ylmethyl)amino | 449 |
| 78 | 3,4-dichlorobenzyl | (pyridin-2-ylmethyl)amino | 449 |

-continued
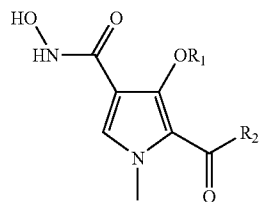
| Example | R1 | R2 | [M + H]+ |
|---|---|---|---|
| 79 | 3,4-dichlorobenzyl | -NH-CH2-(4-pentylphenyl) | 518 |
| 80 | 3,4-dichlorobenzyl | -NH-CH2CH2-S-CH2-(2-chloro-6-fluorophenyl) | 560 |
| 81 | 3,4-dichlorobenzyl | -NH-CH2CH2-S-CH2-(2,6-dichlorophenyl) | 576 |
| 82 | 3,4-dichlorobenzyl | -NH-CH2CH2CH2-O-(4-acetamidophenyl) | 549 |
| 83 | 3,4-dichlorobenzyl | -NH-CH2-(1-methylpyrrol-2-yl) | 451 |
| 84 | 3,4-dichlorobenzyl | -NH-CH2-(2-phenylthiazol-4-yl) | 531 |

-continued
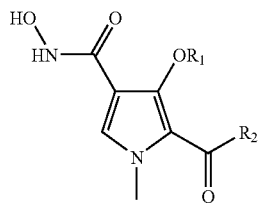
| Example | R1 | R2 | [M + H]+ |
|---|---|---|---|
| 85 | 3,4-dichlorobenzyl | -NH-CH2CH2-S-CH2-(5-((dimethylamino)methyl)furan-2-yl) | 555 |
| 86 | 3,4-dichlorobenzyl | 4-(methoxycarbonyl)benzylamino | 506 |
| 87 | 3,4-dichlorobenzyl | 4-methylbenzylamino | 462 |
| 88 | 3,4-dichlorobenzyl | -NH-CH2CH2-S-(2-(trifluoromethyl)quinolin-4-yl) | 613 |
| 89 | 3,4-dichlorobenzyl | 3-(1H-pyrrol-1-yl)benzylamino | 513 |
| 90 | 3,4-dichlorobenzyl | 4-(1,2,3-thiadiazol-4-yl)benzylamino | 532 |

-continued
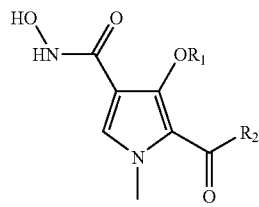
| Example | R1 | R2 | [M + H]+ |
|---|---|---|---|
| 91 | 3,4-dichlorobenzyl | 4-(thiophen-3-yl)benzylamino | 530 |
| 92 | 3,4-dichlorobenzyl | 2,3-dihydro-1,4-benzodioxin-6-ylmethylamino | 506 |
| 93 | 3,4-dichlorobenzyl | (2-chloro-6-phenoxybenzyl)amino | 574 |
| 94 | 3,4-dichlorobenzyl | 4-(dimethylamino)benzylamino | 491 |
| 95 | 2,3-dichlorobenzyl | 4-(dimethylamino)benzylamino | 491 |
| 96 | 3,4-dichlorobenzyl | 1-benzylpiperidin-4-ylamino | 499 |

Example 1

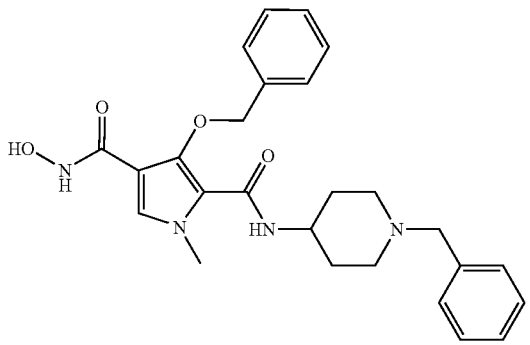

3-Benzyloxy-1-methyl-1H-pyrrole-2,4-dicarboxylic acid 2-[(1-benzyl-piperidin-4-yl)-amide]4-hydroxyamide Example 1 is Prepared in the Following Steps (a–g):

a) 3-Hydroxy-1-methyl-1-H-pyrrole-2,4-dicarboxylic acid 2-ethyl ester. To a solution of 3-hydroxy-1-methyl-1-H-pyrrole-2,4-dicarboxylic acid diethyl ester (30 g, 0.124 mol), prepared according to Chem. Farm. Bull. 1978, 26, 2224, in absolute ethanol (250 mL) is added a solution of sodium hydroxide (24.9 g) in absolute ethanol (900 mL) and the reaction mixture is refluxed for 3 hrs. Water (300 mL) is added and the mixture is refluxed for additional 12 hrs. After removal of ethanol cold water (200 mL) is added and the resulting mixture is acidified with conc. HCl to pH 5. The precipitate is collected by filtration, washed with water and dried. The crude product is purified by crystallization from acetone/EtOH/water to give the desired product (23.28 g, 87%) as a white crystalline powder: mp 211.5° C.; $^1$H NMR (CDCl$_3$) δ 1.40 (t, J=7.2 Hz, 3H), 3.84 (s, 3H), 4.40 (q, J=7.0 Hz, 2H), 7.19 (s, 1H), 8.78 (s, OH); MS m/z 236 [M+Na]$^+$.

b) 3-Hydroxy-1-methyl-1-H-pyrrole-2,4-dicarboxylic acid 4-benzotriazol-1-yl ester 2-ethyl ester. To a stirred solution of 3-hydroxy-1-methyl-1-H-pyrrole-2,4-dicarboxylic acid 2-ethyl ester (10.65 g, 50 mmol) in 200 mL of CH$_2$Cl$_2$ is added 1-hydroxybenzotriazole (8.53 g, 60 mmol) followed by 1.0M solution of dicyclohexyl-carbodiimide (60 mL) in CH$_2$Cl$_2$ and the reaction mixture is stirred at a room temperature for 2 hrs. White precipitate of urea is filtered off and the filtrate is concentrated. The residue is stirred with hexane (100 mL) for several minutes and the precipitated product is collected by filtration. The crude product is crystallized from CH$_2$Cl$_2$/ether to give the title compound (12.8 g, 78%) as a colorless solid: mp 139.1° C.; $^1$H NMR (CDCl$_3$) δ 1.43 (t, J=7.3 Hz, 3H), 3.91 (s, 3H), 4.46 (q, J=7.2 Hz, 2H), 7.36–7.55 (m, 4H), 8.07 (d, J=8.6 Hz, 1H), 8.86(s, OH); MS m/z 331 [M+H]$^+$.

c) 3-Hydroxy-1-methyl-4-trityloxycarbamoyl-1-H-pyrrole-2-carboxylic acid ethyl ester. A mixture of 3-hydroxy-1-methyl-1-H-pyrrole-2,4-dicarboxylic acid 4-benzotriazol-1-yl ester 2-ethyl ester (3.30 g, 10 mmol), 95% pure O-tritylhydroxylamine (3.48 g, 12 mmol) in chloroform (25 mL) is refluxed for 12 hrs. The precipitate is filtered off, washed with CH$_2$Cl$_2$. Water (50 mL) is added to the filtrate and the mixture is shaken well. The pH is adjusted to 7–7.5 and the mixture is shaken again. Organic layer is separated, dried over MgSO$_4$ and concentrated. The residue is crystallized from CH$_2$Cl$_2$/ether to give 2.12 g (45%) of the title compound as white crystalline powder: mp 182.5° C.; $^1$H NMR (CDCl$_3$) δ 1.35 (t, J=7.4 Hz, 3H), 3.69 (s, 3H), 4.33 (q, J=7.0 Hz, 2H), 7.07 (s, 1H), 7.26–7.35 (m, 9H), 7.53–7.55 (m, 6H), 8.55 (br.s, OH), 8.67 (br.s, NH); MS m/z 493 [M+Na]$^+$.

d) 3-Benzyloxy-1-methyl-4-trityloxycarbamoyl-1-H-pyrrole-2-carboxylic acid ethyl ester. A mixture of 3-hydroxy-1-methyl-4-trityloxycarbamoyl-1-H-pyrrole-2-carboxylic acid ethyl ester (470 mg, 1 mmol), potassium carbonate (70 mg, 0.5 mmol) and benzyl chloride (140 mg, 1.1 mmol) in 30 mL of acetone is refluxed for 48 hrs. An inorganic precipitate is filtered off, washed with CH$_2$Cl$_2$. The filtrate is concentrated, the crude residue is chromatographed on silica gel with CHCl$_3$/MeOH=50/1 mixture giving a target compound (360 mg, 64%) as a white crystalline powder: mp 177.2° C.; $^1$H NMR (CDCl$_3$) δ 1.26 (t, J=7.3 Hz, 6H), 3.80 (s, 3H), 4.27 (q, J=7.2 Hz, 2H), 4.84 (s, 2H), 7.10–7.12 (m, 3H), 7.18–7.22 (m, 9H), 7.33–7.39 (m, 9H), 8.88 (s, NH); MS m/z 561 [M+H]$^+$.

e) 3-Benzyloxy-1-methyl-4-trityloxycarbamoyl-1-H-pyrrole-2-carboxylic acid. A mixture of 3-benzyloxy-1-methyl-4-trityloxycarbamoyl-1-H-pyrrole-2-carboxylic acid ethyl ester (280 mg, 0.5 mmol) and 2.5 mL of 1N NaOH in 3 mL of 1,4-dioxane is stirred at 65° C. for 24 hrs. Then the reaction mixture is diluted with 25 mL of water and acidified with 10% citric acid solution to pH 4–5. The obtained precipitate is collected by filtration, washed with water, dried in vacuum. The crude product is crystallized from chloroform/hexane mixture to give 242 mg (91%) of the title compound: mp 131.6° C.; $^1$H NMR (CDCl$_3$) δ 3.79 (s, 3H), 4.90 (s, 2H), 7.08–7.13 (m, 3H), 7.21–7.43 (m, 18H), 8.59 (s, NH); MS m/z 555 [M+Na]$^+$.

f) 3-Benzyloxy-1-methyl-1H-pyrrole-2,4-dicarboxylic acid 2-[(1-benzyl-piperidin-4-yl)-amide]4-(trityloxyamide). To a solution of 3-benzyloxy-1-methyl-4-trityloxycarbamoyl-1-H-pyrrole-2-carboxylic acid (266 mg, 0.5 mmol) in 10 mL of CH$_2$Cl$_2$ are added 1-hydroxybenzotriazole (68 mg, 0.5 mmol), 1-[3-(dimethylamino)-propyl]-3-ethylcarbodiimide hydrochloride (105 mg, 0.55 mmol) and N,N-diisopropylethylamine (65 mg, 0.5 mmol) and the reaction mixture is stirred at a room temperature for 2 hrs. 4-Amino-1-benzyl-piperedine (114 mg, 0.6 mmol) in 1 mL of dichloromethane is added and the reaction mixture is stirred at a room temperature for 3 hrs. Then it is poured into water, aqueous layer is extracted with dichloromethane and combined organic layers are dried over MgSO$_4$ and concentrated. The residue is chromatographed on silica gel with CHCl$_3$/MeOH=25/1 mixture giving the desired compound (320 mg, 91%) as a white crystalline powder: mp 170.9° C.; $^1$H NMR (CDCl$_3$) δ 1.19–1.29 (m, 2H), 1.73–1.76 (m, 2H), 2.046 (t, J=10.6 Hz, 2H), 2.66–2.68 (m, 2H), 3.41 (s, 3H), 3.77–3.81 (m, 4H), 4.70 (s, 2H), 6.75 (d, J=8.11 Hz, 1H), 6.91 (s, 1H), 7.08(m, 2H), 7.23–7.35 (m, 17H), 7.43–7.45 (m, 6H), 8.24 (s, NH); MS m/z 705 [M+H]$^+$.

g) 3-Benzyloxy-1-methyl-1H-pyrrole-2,4-dicarboxylic acid 2-[(1-benzyl-piperidin-4-yl)-amide]4-hydroxyamide. A mixture of 3-benzyloxy-1-methyl-1H-pyrrole-2,4-dicarboxylic acid 2-[(1-benzyl-piperidin-4-yl)-amide]4-(trityloxy-amide) (107 mg, 0.151 mmol) and 2 mL of TFA/CH$_2$Cl$_2$/TIPS=20%/75%/5% mixture is stirred at room temperature for 2 hrs. Then 0.5 mL of 1M HCl solution in ether and 5 mL of ether are added. The precipitated salt is collected by filtration, washed with ether and purified by preparative HPLC to give TFA salt of the title compound (49 mg, 56%) as a white precipitate: mp 92.2° C.; $^1$H NMR (Me$_2$SO-d$_6$) δ 1.22–1.31 (br. m, 2H), 1.65–1.80 (br. m, 2H), 2.32–2.67 (m, 4H), 3.32 (s, 2H), 3.71 (m, 1H), 3.76 (s, 3H), 5.21 (s, 2H), 7.12–7.51 (m, 12H), 8.85 (ex s, 1H), 10.50 (ex s, 1H); MS m/z 463 [M+H]$^+$.

Examples 2–96

Examples 2–96 are prepared according to the procedure described for Example 1 using the appropriate aryl halides and amines in steps 1f and 1d respectively.

EXAMPLES 97–99

The following chart shows the structure of compounds made according to the description for Examples 97–99 described below:

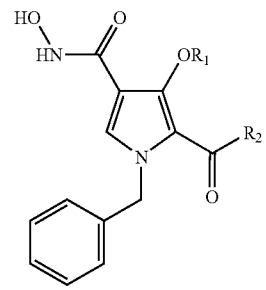

| Example | R1 | R2 | [M + H]$^+$ |
|---|---|---|---|
| 97 | 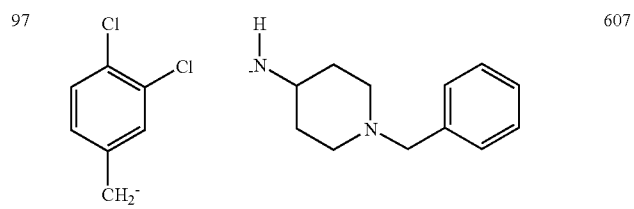 | | 607 |
| 98 | 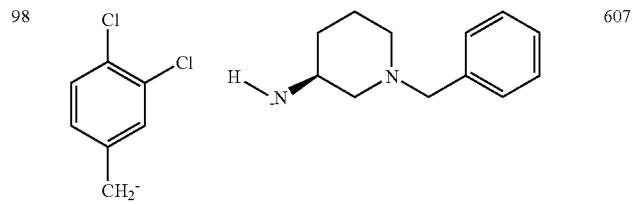 | | 607 |
| 99 | 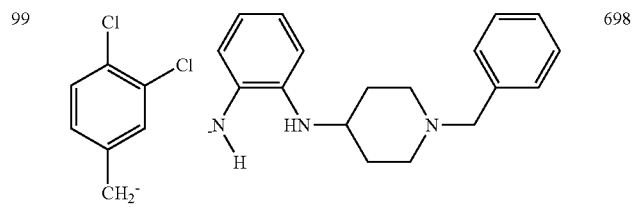 | | 698 |

Example 97

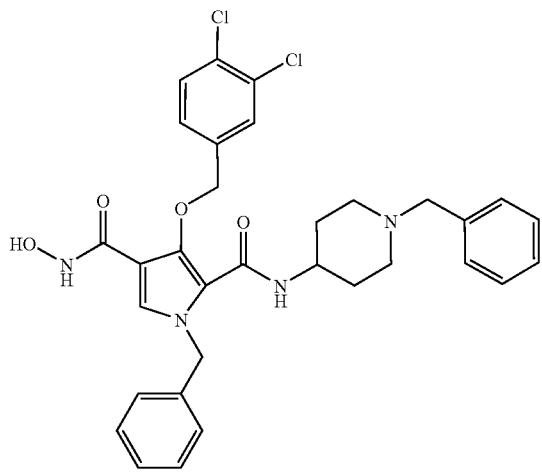

1-Benzyl-3-(3,4-dichloro-benzyloxy)-1H-pyrrole-2,
4-dicarboxylic acid 2-[(1-benzyl-piperidin-4-yl)-
amide]4-hydroxyamide a) 1-Benzyl-3-hydroxy-1H-pyrrole-2,4-dicarboxylic acid 2-ethyl ester. To a solution of 1-benzyl-3-hydroxy-1H-pyrrole-2,4-dicarboxylic acid diethyl ester (20.6 g, 65 mmol), prepared according to Chem. Farm. Bull. 1978, 26, 2224, in absolute ethanol (150 mL) is added a solution of sodium hydroxide (20.0 g, 0.5 mol) in absolute ethanol (750 mL) and the reaction mixture is refluxed for 1 hr. Water (200 mL) is added and the mixture is stirred at 65° C. for additional 12 hrs. After removal of ethanol cold water (200 mL) is added and the resulting mixture is acidified with conc. HCl to pH 5. The precipitate is collected by filtration, washed with water and dried to give the desired product (16.2 g, 86%) as a white crystalline powder: MS m/z 290 [M+H]$^+$.

b) 1-Benzyl-3-hydroxy-4-trityloxycarbamoyl-1H-pyrrole-2-carboxylic acid ethyl ester. To a stirred solution of 1-benzyl-3-hydroxy-1H-pyrrole-2,4-dicarboxylic acid 2-ethyl ester (5.00 g, 17.3 mmol) in 50 mL of CH$_2$Cl$_2$ are added 1-hydroxybenzotriazole (2.80 g, 20.8 mmol), 1-[3-(dimethylamino)-propyl]-3-ethylcarbodiimide hydrochloride (3.99 g, 20.8 mmol) and the reaction mixture is stirred at a room temperature for 2 hrs. 95% Pure O-trityl-hydroxylamine (6.00 g, 20.8 mmol) and N,N-diisopropylethylamine (5.58 g, 43.25 mmol) are added and the resulting mixture is stirred at room temperature for 48 hrs. Then it is poured into water, aqueous layer is extracted with dichloromethane and combined organic layers are dried over MgSO$_4$ and concentrated. The residue is chromatographed on silica gel with hexane/ethyl acetate=8/2 mixture giving the desired compound (5.86 g, 62%) as a white crystalline powder: MS m/z 547 [M+H]$^+$.

c) 1-Benzyl-3-(2,4-dichloro-benzyloxy)-4-trityloxycarbamoyl-1H-pyrrole-2-carboxylic acid ethyl ester. A mixture of 1-benzyl-3-hydroxy-4-trityloxycarbamoyl-1H-pyrrole-2-carboxylic acid ethyl ester (2.61 g, 4.8 mmol), potassium carbonate (330 mg, 2.4 mmol) and 3,4-dichlorobenzyl chloride (1.03 g, 5.3 mmol) in 70 mL of acetone is refluxed for 24 hrs. An inorganic precipitate is filtered off, washed with CH$_2$Cl$_2$. The filtrate is concentrated, the crude residue is chromatographed on silica gel with hexane/ethyl acetate=4/ 1, 3/2 mixtures giving a target compound (2.61 g, 77%) as a white crystalline powder: MS m/z 705 [M+H]$^+$.

d) 1-Benzyl-3-(2,4-dichloro-benzyloxy)-4-trityloxycarbamoyl-1H-pyrrole-2-carboxylic acid. A mixture of 1-benzyl-3-(2,4-dichloro-benzyloxy)-4-trityloxycarbamoyl-1H-pyrrole-2-carboxylic acid ethyl ester (2.46 g, 3.48 mmol) and 20 mL of 1N NaOH in 1,4-dioxane/methanol=8 mL/8 mL is stirred at 65° C. for 24 hrs. Then the reaction mixture is diluted with 50 mL of water and acidified with 10% citric acid solution to pH 5–6. The obtained precipitate is collected by filtration, washed with water, dried in vacuum to give 2.20 g (93%) of the title compound. MS m/z 677 [M+H]$^+$.

e) 1-Benzyl-3-(3,4-dichloro-benzyloxy)-1H-pyrrole-2,4-dicarboxylic acid 2-[(1-benzyl-piperidin-4-yl)-amide]4-(trityloxy-amide). To a solution of 1-benzyl-3-(2,4-dichloro-benzyloxy)-4-trityloxycarbamoyl-1H-pyrrole-2-carboxylic acid (300 mg, 0.44 mmol) in 10 mL of CH$_2$Cl$_2$ are added 1-hydroxybenzotriazole (66 mg, 0.49 mmol), 1-[3-(dimethylamino)-propyl]-3-ethylcarbodiimide hydrochloride (93 mg, 0.49 mmol) and N,N-diisopropylethylamine (126 mg, 0.97 mmol) and the reaction mixture is stirred at a room temperature for 1 hr. 4-Amino-1-benzyl-piperidine (101 mg, 0.53 mmol) is added and the reaction mixture is stirred at a room temperature for 3 hrs. Then it is poured into water, pH of an aqueous layer is adjusted to 9 with 1N NaOH and the mixture is shaken well. Then the pH is adjusted to 7 with 4N HCl and the mixture is shaken well again. Organic layer is separated and the aqueous layer is extracted with CH$_2$Cl$_2$. Combined organic layers are dried over MgSO$_4$ and concentrated. The residue is chromatographed on silica gel with hexane/ethyl acetate=4/1 mixture giving the desired compound (320 mg, 85%) as a white crystalline powder: MS m/z 849 [M+H]$^+$.

f) 1-Benzyl-3-(3,4-dichloro-benzyloxy)-1H-pyrrole-2,4-dicarboxylic acid 2-[(1-benzyl-piperidin-4-yl)-amide]4-hydroxyamide. A mixture of 1-benzyl-3-(3,4-dichloro-benzyloxy)-1H-pyrrole-2,4-dicarboxylic acid 2-[(1-benzyl-piperidin-4-yl)-amide]4-(trityloxy-amide) (120 mg, 0.14 mmol) and 2 mL of TFA/CH$_2$Cl$_2$/TIPS=20%/75%/5% mixture is stirred at room temperature for 2 hrs. Then 0.3 mL of 1M HCl solution in ether and 5 mL of ether are added. The precipitated salt is collected by filtration, washed with ether and purified by preparative HPLC to give TFA salt of the title compound (82 mg, 81%) as a white precipitate: MS m/z 607 [M+H]$^+$.

Example 98

1-Benzyl-3-(3,4-dichloro-benzyloxy)-1H-pyrrole-2,4-dicarboxylic acid 2-[(1-benzyl-piperidin-3-yl)-amide]4-hydroxyamide. Example 98 is prepared according to the procedure described for Example 97 using (S)-(+)-1-benzyl-3-aminopiperidine in place of 4-amino-1-benzyl-piperidine in step 97e. Obtained in the form of an HCl salt after deprotection step as a white precipitate: yield 68%; MS m/z 607 [M+H]$^+$.

Example 99

1-Benzyl-3-(3,4-dichloro-benzyloxy)-1H-pyrrol-2,4-dicarboxylic acid 2-{[2- (1-benzyl-piperidin-4-ylamino)-phenyl]-amide}4-hydroxyamide. Example 99 is prepared according to the procedure described for Example 97 using N1-(1-benzyl-4-piperidyl)benzene-1,2-diamine in place of 4-amino-1-benzyl-piperidine in step 97e. yield 71%; MS m/z 698 [M+H]$^+$.

EXAMPLES 100–122

The following chart shows the structures of compounds made according to the description in Examples 100 described below:

| Example | R1 | R2 | [M + H]$^+$ |
|---|---|---|---|
| 100 | benzyl (CH$_2$-phenyl) | NH-(1-benzylpiperidin-4-yl) | 463 |
| 101 | benzyl (CH$_2$-phenyl) | NH-CH$_2$CH$_2$CH$_2$-(4-methylpiperazin-1-yl) | 430 |
| 102 | 4-methoxybenzyl | NH-(1-benzylpiperidin-4-yl) | 493 |
| 103 | 4-methoxybenzyl | 4-benzylpiperazin-1-yl | 479 |
| 104 | 4-methoxybenzyl | NH-(1-benzylpiperidin-3-yl) | 493 |
| 105 | 2,3-dichlorobenzyl | NH-CH$_2$-(4-dimethylaminophenyl) | 491 |

-continued
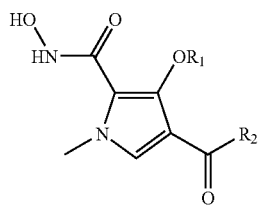
| Example | R1 | R2 | [M + H]+ |
|---|---|---|---|
| 106 | 3,4-dichlorobenzyl | 1-benzylpiperidin-4-ylamino | 531 |
| 107 | 3,4-dichlorobenzyl | 4-benzylpiperazin-1-yl | 517 |
| 108 | 3,4-dichlorobenzyl | 1-benzylpiperidin-3-ylamino | 531 |
| 109 | 3,4-dichlorobenzyl | 1-benzylpyrrolidin-3-ylamino | 517 |
| 110 | 2,3-dichlorobenzyl | 1-benzylpiperidin-4-ylamino | 531 |
| 111 | 2,3-dichlorobenzyl | 4-benzylpiperazin-1-yl | 517 |
| 112 | 2,3-dichlorobenzyl | 1-benzylpiperidin-3-ylamino | 531 |

-continued
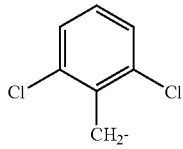
| Example | R1 | R2 | [M + H]+ |
|---|---|---|---|
| 113 | 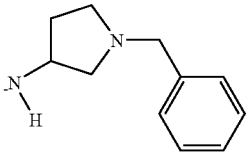 |  | 517 |
| 114 | 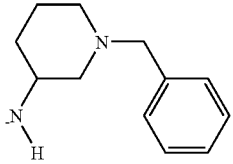 |  | 488 |
| 115 | 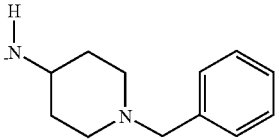 | 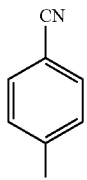 | 488 |
| 116 | 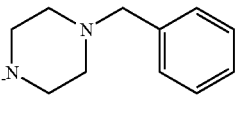 | 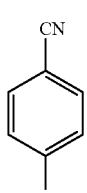 | 474 |
| 117 | 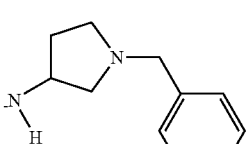 | 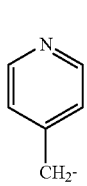 | 474 |
| 118 | 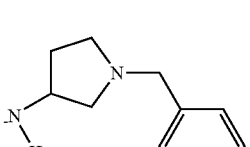 | 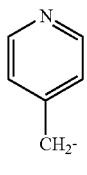 | 450 |
| 119 | 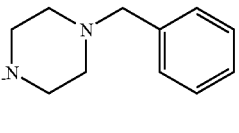 | | 450 |

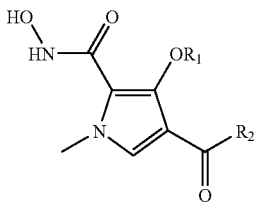

| Example | R1 | R2 | [M + H]+ |
|---|---|---|---|
| 120 | 4-pyridyl-CH2- | 1-benzyl-piperidin-4-yl-NH- | 464 |
| 121 | 4-pyridyl-CH2- | 1-benzyl-piperidin-3-yl-NH- | 464 |
| 122 | 3,4-difluorophenyl-CH2- | 1-benzyl-piperidin-4-yl-NH- | 499 |

Example 100

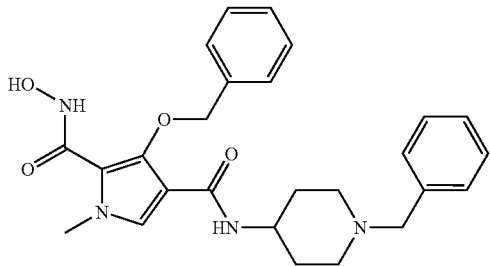

3-Benzyloxy-1-methyl-1H-pyrrole-2,4-dicarboxylic acid 4-[(1-benzyl-piperidine-4-yl)-amide]2-hydroxyamide a) 4-(1-Benzyl-piperidin-4-ylcarbamoyl)-3-hydroxy-1-methyl-1H-pyrrole-2-carboxylic acid ethyl ester. A mixture of 3-hydroxy-1-methyl-1-H-pyrrole-2, 4-dicarboxylic acid 4-benzotriazol-1-yl ester 2-ethyl ester (1.50 g, 4.53 mmol) and 4-amino-1-benzyl-piperidine (0.91 g, 4.79 mmol) in CH2Cl2 (30 mL) is stirred at a room temperature for 2 hrs. The reaction mixture is diluted with 120 mL of CH2Cl2 and 150 mL of water is added; pH of an aqueous layer is adjusted to 9 with 1N NaOH and the mixture is shaken well. Then the pH is adjusted to 7 with 4N HCl and the mixture is shaken well again. Organic layer is separated and the aqueous layer is extracted with CH2Cl2 (2×50 mL). The combined organic layers are dried over MgSO4 and concentrated. The residue is chromatographed on silica gel with CHCl3/MeOH=20/1, 15/1 mixture giving the desired compound (1.66 g, 95%) as a white crystalline powder: mp 146.3° C.; $^1$H NMR (CDCl3) δ 1.40 (t, J=7.4 Hz, 3H), 1.56–1.66 (m, 2H), 1.97–2.01 (m, 2H), 2.25 (t, J=10.8 Hz, 2H), 2.86 (m, 2H), 3.56 (s, 2H), 3.77 (s, 3H), 3.91–4.03 (m, 1H), 4.39 (q, J=7.2 Hz, 2H), 6.70 (d, J=7.8 Hz, NH), 7.15 (s, 1H), 7.21–7.33 (m, 5H), 8.89 (br.s, OH); MS m/z 386 [M+H]+.

b) 3-Benzyloxy-4-(1-benzyl-piperidin-4-ylcarbamoyl)-1-methyl-1H-pyrrole-2-carboxylic acid ethyl ester. A mixture of 4-(1-benzyl-piperidin-4-ylcarbamoyl)-3-hydroxy-1-methyl-1H-pyrrole-2-carboxylic acid ethyl ester (500 mg, 1.30 mmol), potassium carbonate (90 mg, 0.65 mmol) and benzyl chloride (180 mg, 1.42 mmol) in 15 mL of acetone is refluxed for 48 hrs. An inorganic precipitate is filtered off, washed with CH2Cl2. The filtrate is concentrated, the crude residue is chromatographed on silica gel with EtOAc/MeOH=9/1,8/2 mixture to give the target compound (400 mg, 65%) as a white crystalline powder: mp 132.3° C.; $^1$H NMR (CDCl3) δ 1.18–1.27 (m, 2H), 1.35 (s, J=7.3 Hz, 3H), 1.73–1.78 (m, 2H), 2.07 (t, J=10.7 Hz, 2H), 2.61 (m, 2H), 3.40 (s, 2H), 3.47–3.85 (m, 1H), 3.88 (s, 3H), 4.36 (q, J=7.2 Hz, 2H), 5.10 (s, 2H), 6.90 (d, J=7.8 Hz, NH), 7.23–7.45 (m, 11H), MS m/z 476 [M+H]+.

c) 3-Benzyloxy-4-(1-benzyl-piperidin-4-ylcarbamoyl)-1-methyl-1H-pyrrole-2-carboxylic acid. A mixture of 3-benzyloxy-4-(1-benzyl-piperidin-4-ylcarbamoyl)-1-methyl-1H-pyrrole-2-carboxylic acid ethyl ester (476 mg, 1 mmol) and 5 mL of 1N NaOH in 5 mL of 1,4-dioxane is stirred at 65° C. for 3 hrs. Then the reaction mixture is diluted with 10 mL of water, acidified with 10% citric acid solution to pH 6–5 and extracted with $CH_2Cl_2$. The combined organic layers are dried over $Na_2SO_4$ and concentrated. The residue is crystallized from $CH_2Cl_2$/ether mixture to give the title compound (361 mg, 96%) as a white crystals: mp 141.9° C.; $^1$H NMR (CDCl$_3$) δ 1.45–1.55 (m, 4H), 2.27 (dt, J=12.0 Hz, J=3.2 Hz, 2H), 3.06–3.09 (m, 2H), 3.66–3.69 (m, 1H), 3.95 (s, 2H), 4.04 (s, 3H), 5.24 (s, 2H), 6.81 (t, J=7.7 Hz, 2H), 7.08 (t, J=7.5 Hz, 1H), 7.18–7.26 (m, 3H), 7.36–7.39 (m, 3H), 7.46–7.49 (m, 2H); MS m/z 448 [M+H]$^+$.

d) 3-Benzyloxy-1-methyl-1H-pyrrole-2,4-dicarboxylic acid 4-[(1-benzyl-piperidin-4-yl)-amide]2-(trityloxy-amide). A mixture of 3-benzyloxy-4-(1-benzyl-piperidin-4-ylcarbamoyl)-1-methyl-1H-pyrrole-2-carboxylic acid (224 mg, 0.50 mmol), 1-hydroxybenzotriazole (81 mg, 0.60 mmol), 1-[3-(dimethylamino)-propyl]-3-ethylcarbodiimide hydrochloride (115 mg, 0.60 mmol) in 15 mL of $CH_2Cl_2$ is stirred at a room temperature for 1 hr. N,N-Diisopropylethylamine (194 mg, 1.5 mmol) and 95% pure O-trityl-hydroxylamine (165 mg, 0.60 mmol) are added and the resulting mixture is stirred at a room temperature for 48 hrs. The reaction mixture is diluted with 15 mL of $CH_2Cl_2$ and washed with water (15 mL). Aqueous layer is extracted with $CH_2Cl_2$ (2×15 mL). The combined organic layers are dried over $Na_2SO_4$ and concentrated. The crude residue is chromatographed on silica gel in CHCl$_3$/MeOH=25/1, 20/1 mixture to give the target compound (204 mg, 58%) as a white crystalline powder: mp 155.1° C.; $^1$H NMR (CDCl$_3$) δ 1.23 (m, 2H), 1.81 (d, J=10.3 Hz, 2H), 2.08 (t, J=10.3 Hz, 2H), 2.71 (d, J=9.7 Hz, 2H), 3.44 (s, 2H), 3.64 (s, 3H), 3.82–3.90 (m, 1H), 4.74 (s, 2H), 6.27 (d, J=7.9 Hz, NH), 7.07–7.15 (m, 3H), 7.21–7.42 (m, 23H), 8.80 (s, NH); MS m/z 705 [M+H]$^+$.

e) 3-Benzyloxy-1-methyl-1H-pyrrole-2,4-dicarboxylic acid 4-[(1-benzyl-piperidin-4-yl)-amide]2-hydroxyamide. A mixture of 3-benzyloxy-1-methyl-1H-pyrrole-2,4-dicarboxylic acid 4-[(1-benzyl-piperidin-4-yl)-amide]2-(trityloxy-amide) (107 mg, 0.148 mmol) and 2 mL of TFA/$CH_2Cl_2$/TIPS=20%/75%/15% mixture is stirred at room temperature for 2 hrs. Then 0.4 mL of 1M HCl solution in ether and 10 mL of ether are added. The precipitated salt is collected by filtration, washed with ether and purified by preparative HPLC to give TFA salt of the title compound (56 mg, 69%) as a white precipitate, mp 98.8° C., MS m/z 463 [M+H]$^+$.

Examples 101–122

Examples 101–122 are prepared according to the procedure described for Example 100 using the appropriate aryl halides and amines in steps 100a and 100b respectively.

EXAMPLES 123–124

The following chart shows the structures of compounds made according to the description in Examples 123 described below:

| Example | R1 | R2 | [M + ]$^+$ |
|---|---|---|---|
| 123 | 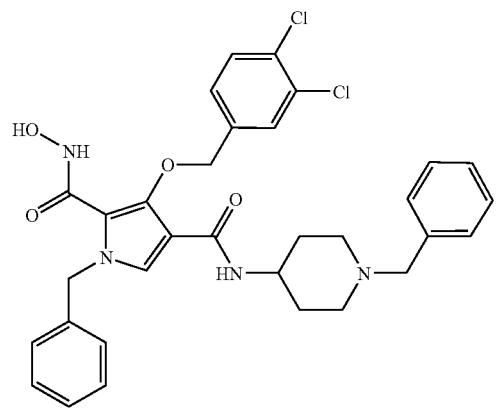 | | 592 |
| 124 | | | 578 |

Example 123

1-Benzyl-3-(3,4-dichloro-benzyloxy)-1H-pyrrole-2,4-dicarboxylic acid 4-[(1-benzyl-piperidin-4-yl)-amide]2-hydroxyamide a) 1-Benzyl-4-(1-benzyl-piperidin-4-ylcarbamoyl)-3-hydroxy-1H-pyrrole-2-carboxylic acid ethyl ester. To a stirred solution of 1-benzyl-3-hydroxy-1H-pyrrole-2,4-dicarboxylic acid 2-ethyl ester (2.90 g, 10 mmol) in 100 mL of CH$_2$Cl$_2$ are added 1-hydroxybenzotriazole (1.50 g, 11 mmol), 1-[3-(dimethylamino)-propyl]-3-ethylcarbodiimide hydrochloride (2.35 g, 12 mmol) and the reaction mixture is stirred at a room temperature for 1 hr. 4-Amino-1-benzyl-piperidine (2.28 g, 12 mmol) is added and the reaction mixture is stirred at a room temperature for 2 hrs. The reaction mixture is diluted with 200 mL of CH$_2$Cl$_2$ and 500 mL of water is added; pH of an aqueous layer is adjusted to 9 with 1N NaOH and the mixture is shaken well. Then the pH is adjusted to 7 with 4N HCl and the mixture is shaken well again. Organic layer is separated and the aqueous layer is extracted with CH$_2$Cl$_2$. The combined organic layers are dried over MgSO4 and concentrated. The residue is chromatographed on silica gel using ethyl acetate as an eluent giving the desired compound (3.23 g, 70%) as a white crystalline powder, MS m/z 462 [M+H]$^+$.

b) 1-Benzyl-4-(1-benzyl-piperidin-4-ylcarbamoyl)-3-(3,4-dichloro-b nzyloxy)-1H-pyrrol-2-carboxylic acid ethyl ester. A mixture of 1-benzyl-4-(1-benzyl-piperidin-4-ylcarbamoyl)-3-hydroxy-1H-pyrrole-2-carboxylic acid ethyl ester (2.31 g, 5 mmol), potassium carbonate (350 mg, 2.5 mmol) and 3,4-dichloro benzyl chloride (1.17 g, 6 mmol) in 50 mL of acetone is refluxed for 48 hrs. An inorganic precipitate is filtered off, washed with CH$_2$Cl$_2$. The filtrate is concentrated, the crude residue is chromatographed on silica gel with chloroform/MeOH=50/1 mixture to give the target compound (2.65 g, 85%) as a white crystalline powder, MS m/z 620 [M+H]$^+$.

c) 1-Benzyl-4-(1-benzyl-piperidin-4-ylcarbamoyl)-3-(3,4-dichloro-benzyloxy)-1H-pyrrole-2-carboxylic acid. A mixture 1-benzyl-4-(1-benzyl-piperidin-4-ylcarbamoyl)-3-(3,4-dichloro-benzyloxy)-1H-pyrrole-2-carboxylic acid ethyl ester (2.48 g, 4 mmol) and 20 mL of 1N NaOH in 1,4-dioxane/methanol=20 mL/20 mL is stirred at 65° C. for 4 hrs. Then the reaction mixture is concentrated to the volume of 20 mL, acidified with 10% citric acid solution to pH 5. The obtained precipitate is collected by filtration, washed with water, dried in vacuum to give 2.13 g (90%) of the title compound. The crude product is used in the next step without further purification: MS m/z 592 [M+H]$^+$.

d) 1-Benzyl-3-(3,4-dichloro-benzyloxy)-1H-pyrrole-2,4-dicarboxylic acid 4-[(1-benzyl-piperidin-4-yl)-amide]2-(trityloxy-amide). A mixture of 1-benzyl-4-(1-benzyl-piperidin-4-ylcarbamoyl)-3-(3,4-dichloro-benzyloxy)-1H-pyrrole-2-carboxylic acid (593 mg, 1 mmol), 1-hydroxybenzotriazole (145 mg, 1 mmol), 1-[3-(dimethylamino)-propyl]-3-ethylcarbodiimide hydrochloride (240 mg, 1.2 mmol) and N,N-diisopropylethylamine (323 mg, 2.5 mmol) in 20 mL of CH$_2$Cl$_2$ is stirred at a room temperature for 30 min. 95% pure O-trityl-hydroxylamine (350 mg, 1.2 mmol) is added and the resulting mixture is stirred at a room temperature for 24 hrs. The reaction mixture is diluted with 20 mL of CH$_2$Cl$_2$ and 40 mL of water is added; pH of an aqueous layer is adjusted to 9 with 1N NaOH and the mixture is shaken well. Then the pH is adjusted to 7 with 4N HCl and the mixture is shaken well again. Organic layer is separated and the aqueous layer is extracted with CH$_2$Cl$_2$. The combined organic layers are dried over MgSO4 and concentrated to give 747 mg (88%) of the target compound. The residue is used in the next step without further purification: MS m/z 849 [M+H]$^+$.

e) 1-Benzyl-3-(3,4-dichloro-benzyloxy)-1H-pyrrole-2,4-dicarboxylic acid 4-[(1-benzyl-piperidin-4-yl)-amide]2-hydroxyamide. A mixture of a crude product from the previous step (200 mg, 0.24 mmol) and 2 mL of TFA/CH$_2$Cl$_2$/TIPS=20%/75%/5% mixture is stirred at room temperature for 1 hrs. Then 0.5 mL of 1M HCl solution in ether and 10 mL of ether are added. The precipitated salt is collected by filtration, washed with ether and purified by preparative HPLC. Yield: 99 mg, (68%) as a white precipitate, MS m/z 607 [M+H]$^+$.

Example 124

1-Benzyl-4-(4-benzyl-piperazine-1-carbonyl)-3-(3,4-dichloro-benzyloxy)-1H-pyrrole-2-carboxylic acid hydroxyamide Example 124 is prepared according to the procedure described for Example 123 using 1-benzylpiperazine in place of 4-amino-1-benzyl-piperidine in step 123a. White crystalline powder after preparative HPLC: yield 48%; MS m/z 593 [M+H]$^+$.

What is claimed is:

1. A compound having the structure of Formula (I) or Formula (II)

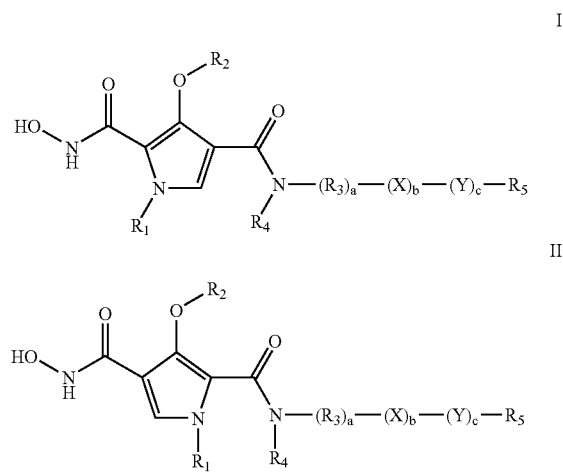

wherein:

$R_1$ is selected from H, substituted and unsubstituted alkyl, substituted and unsubstituted aryl, substituted and unsubstituted arylalkyl, substituted and unsubstituted heteroarylalkyl, and substituted and unsubstituted cycloalkyl;

$R_2$ is selected from H, substituted and unsubstituted alkyl, substituted and unsubstituted alkenyl, substituted and unsubstituted alkynyl, substituted and unsubstituted heteroalkyl, substituted and unsubstituted aryl, substituted and unsubstituted arylalkyl, substituted and unsubstituted heteroarylalkyl, and substituted and unsubstituted cycloalkyl;

$R_3$ is selected from a substituted and unsubstituted alkyl or a substituted and unsubstituted heteroalkyl;

$R_4$ is selected from H, substituted and unsubstituted alkyl, substituted and unsubstituted heteroalkyl, substituted and unsubstituted aryl, substituted and unsubstituted arylalkyl, substituted and unsubstituted heteroarylalkyl, and substituted and unsubstituted cycloalkyl;

$R_3$ and $R_4$ can be connected together to form a pyridine or piperidine ring;

$R_5$ is selected from H, substituted and unsubstituted alkyl, substituted and unsubstituted heteroalkyl, substituted and unsubstituted aryl, substituted and unsubstituted arylalkyl, substituted and unsubstituted pyridine, substituted and unsubstituted cycloalkyl, and substituted and unsubstituted piperidine;

X and Y are independently selected from substituted and unsubstituted alkyl, substituted and unsubstituted alkenyl, substituted and unsubstituted alkynyl, substituted and unsubstituted heteroalkyl, substituted and unsubstituted haloalkyl, substituted and unsubstituted aryl, substituted and unsubstituted arylalkyl, substituted and unsubstituted pyridine, substituted and unsubstituted cycloalkyl, substituted and unsubstituted piperidine, $CO_2$, CO and $SO_2$, wherein a, b and c are each independently 0 or 1, and including pharmaceutically acceptable salts thereof.

2. The compound of claim 1, wherein $R_1$ is —H, lower substituted and unsubstituted alkyl, substituted and unsubstituted benzyl, substituted and unsubstituted alkoxybenzyl, substituted and unsubstituted dialkylamino alkyl.

3. The compound of claim 2, wherein $R_1$ is methyl or substituted and unsubstituted benzyl.

4. The compound of claim 1, wherein $R_2$ is —H, lower substituted and unsubstituted alkyl, substituted and unsubstituted arylalkyl, or.

5. The compound of claim 4, wherein $R_2$ is substituted or unsubstituted arylalkyl with 0–4 substituents selected from alkoxy, F, Cl, Br, CN, 2,4-dichloro, 3,4-dichloro, 2,6-dichloro, and 3,4-difluoro.

6. The compound of claim 1, wherein $R_3$ is selected from substituted and unsubstituted alkyl or substituted and unsubstituted heteroalkyl.

7. The compound of claim 1, wherein $R_4$ is —H or substituted or unsubstituted lower alkyl.

8. The compound of claim 1, wherein $R_4$ and $R_3$ form a pyridine ring.

9. The compound of claim 1, wherein $R_4$ and $R_3$ form a piperidine ring.

10. The compound of claim 1, wherein X is alkyl, heterolakyl, or aryl.

11. The compound of claim 1, wherein X is pyridine.

12. The compound of claim 1, wherein X is piperidine.

13. The compound of claim 1, wherein Y is bond, alkyl, aryl, or COO.

14. The compound of claim 1, wherein Y is pyridine or piperidine.

15. The compound of claim 13, wherein Y is COO.

16. The compound of claim 1, wherein $R_5$ is —H, substituted and unsubstituted alkyl, substituted and unsubstituted heteroalkyl, and substituted and unsubstituted aryl.

17. The compound of claim 16, wherein $R_5$ is aryl or substituted aryl.

18. The compound of claim 17, wherein $R_5$ is phenyl or benzyl.

19. A pharmaceutical composition comprising a therapeutically effective amount of a compound of claim 1 in a pharmaceutically-acceptable carrier.

20. A method for treating colon cancer in a mammal comprising administering to said mammal a therapeutically effective amount of a compound of claim 1.

21. A compound, including pharmaceutically acceptable salts thereof, having the structure of:

3-Benzyloxy-1-methyl-1H-pyrrole-2,4-dicarboxylic acid 2-[(1-benzyl-piperidin-4-yl)-amide]4-hydroxyamide, 3-Benzyloxy-1-methyl-1H-pyrrole-2,4-dicarboxylic acid 2-(4-dimethylamino-benzylamide) 4-hydroxyamide, 3-Benzyloxy-1-methyl-1H-pyrrole-2,4-dicarboxylic acid 2-[(3-dimethylamino-2,2-dimethyl-propyl)-amide]4-hydroxyamide, 3-(4-Methoxy-benzyloxy)-1-methyl-1H-pyrrole-2,4-dicarboxylic acid 2-(4-dimethylaminobenzylamide)4-hydroxyamide, 3-(4-Methoxy-benzyloxy)-1-methyl-1H-pyrrole-2,4-dicarboxylic acid 2-[(1-benzyl-piperidin-4-yl)-amide]4-hydroxyamide, 3-(3,4-Dichloro-benzyloxy)-1-methyl-1H-pyrrole-2,4-dicarboxylic acid 2-(4-dimethylamino-benzylamide)4-hydroxyamide, 3-(3,4-Dichloro-benzyloxy)-1-methyl-1H-pyrrole-2,4-dicarboxylic acid 4-hydroxyamide 2-{[3-(2-methyl-piperidin-1-yl)-propyl]-amide}, 3-(3,4-Dichloro-benzyloxy)-1-methyl-1H-pyrrole-2,4-dicarboxylic acid 2-[(3-dimethylamino-propyl)-amide]4-hydroxyamide, 3-(3,4-Dichloro-benzyloxy)-1-methyl-1H-pyrrole-2,4-dicarboxylic acid 2-[(3-dimethylamino-2,2-dimethyl-propyl)-amide]4-hydroxyamide, 3-(3,4-Dichloro-benzyloxy)-1-methyl-1H-pyrrole-2,4-dicarboxylic acid 4-hydroxyamide 2-[(3-piperidin-1-yl-propyl)-amide], 3-(3,4-Dichloro-benzyloxy)-1-methyl-1H-pyrrole-2,4-dicarboxylic acid 2-[(3-diethylamino-propyl)-amide]4-hydroxyamide, 3-(3,4-Dichloro-benzyloxy)-1-methyl-1H-pyrrole-2,4-dicarboxylic acid 2-[(3-dibutylamino-propyl)-amide]4-hydroxyamide, 3-(3,4-Dichloro-benzyloxy)-1-methyl-1H-pyrrole-2,4-dicarboxylic acid 2-(4-amino-benzylamide)4-hydoxyamide, 3-(3,4-Dichloro-benzyloxy)-1-methyl-1H-pyrrole-2,4-dicarboxylic acid 2-[(2-diethylamino-ethyl)-amide]4-hydroxyamide, 3-(3,4-Dichloro-benzyloxy)-1-methyl-1H-pyrrole-2,4-dicarboxylic acid 2-[(1-benzyl-piperidin-4-yl)-amide]4-hydroxyamide, 3-(3,4-Dichloro-benzyloxy)-1-methyl-1H-pyrrole-2,4-dicarboxylic acid 4-hydroxyamide 2-{[3-(4-methyl-piperazin-1-yl)-propyl]-amide}, 3-(3,4-Dichloro-benzyloxy)-1-methyl-1H-pyrrole-2,4-dicarboxylic acid 2-(4-aminomethyl-benzylamide)4-hydroxyamide, 6-{[3-(3,4-Dichloro-benzyloxy)$_4$-hydroxycarbamoyl-1-methyl-1H-pyrrole-2-carbonyl]-amino}-hexanoic acid methyl ester, 3-(3,4-Dichloro-benzyloxy)-1-methyl-1H-pyrrole-2,4-dicarboxylic acid 2-(3,4-dihydroxy-benzylamide)4-hydroxyamide, 3-(3,4-Dichloro-benzyloxy)$_4$-hydroxycarbamoyl-1-methyl-1H-pyrrole-2-carboxylic acid 1-benzyl-piperidin-4-yl ester, 5-([1,4']Bipiperidinyl-1'-carbonyl)-4-(3,4-dichloro-benzyloxy)-1-methyl-1H-pyrrole-3-carboxylic acid hydroxyamide, 3-(3,4-Dichloro-benzyloxy)-1-methyl-1H-pyrrole-2,4-dicarboxylic acid 4-hydroxyamide 2-[(1-naphthalen-1-yl-ethyl)-amide], 3-(3,4-Dichloro-benzyloxy)-1-methyl-1H-pyrrole-2,4-dicarboxylic acid 2-[(benzo[1,3]dioxol-5-ylmethyl)-amide]4-hydroxyamide, 3-(3,4-Dichloro-benzyloxy)-1-methyl-1H-pyrrole-2,4-dicarboxylic acid 4-hydroxyamide 2-{[(4-methyl-pyridin-2-yl)-phenyl-methyl]-amide}, 5-(N'-Benzyl-hydrazinocarbonyl)-4-(3,4-dichloro-benzyloxy)-1-methyl-1H-pyrrole-3-carboxylic acid hydroxyamide, 3-(3,4-Dichloro-benzyloxy)-1-methyl-1H-pyrrole-2,4-dicarboxylic acid 2-{[2-(1-benzyl-piperidin-4-ylamino)-phenyl]-amide}4-hydroxyamide, 3-(3,4-Dichloro-benzyloxy)-1-methyl-1H-pyrrole-2,4-dicarboxylic acid 4-hydroxyamide 2-{[4-(4-methyl-piperidin-1-yl)-phenyl]-amide}, 3-(3,4-Dichloro-benzyloxy)-1-methyl-1H-pyrrole-2,4-dicarboxylic acid 4-hydroxyamide 2-piperidin-4-ylamide, 5-(4-Amino-piperidine-1-carbonyl)-4-(3,4-dichloro-benzyloxy)-1-methyl-1H-pyrrole-3-carboxylic acid hydroxyamide, 3-(3,4-Dichloro-benzyloxy)-1-methyl-1H-pyrrole-2,4-dicarboxylic acid 2-{[1-(4-dimethylamino-butyryl)-piperidin-4-yl]-amide}4-hydroxyamide, 3-(3,4-Dichloro-benzyloxy)-1-methyl-1H-pyrrole-2,4-dicarboxylic acid 2-{[1-(4-cyano-benzyl)-piperidin-4-yl]-amide}4-hydroxyamide, 3-(3,4-Dichloro-benzyloxy)-1-methyl-1H-pyrrole-2,4-dicarboxylic acid 4-hydroxyamide 4-[(1,2,2,6,6-pentamethyl-piperidin-4-yl)-amide], 4-{[3-(3,4-Dichloro-benzyloxy)₄-hydroxycarbamoyl-1-methyl-1H-pyrrole-2-carbonyl]-amino}-piperidine-1-carboxylic acid ethyl ester, 3-(3,4-Dichloro-benzyloxy)-1-methyl-1H-pyrrole-2,4-dicarboxylic acid 4-hydroxyamide 2-indan-1-ylamide, 3-(3,4-Dichloro-benzyloxy)-1-methyl-1H-pyrrole-2,4-dicarboxylic acid 2-[(9H-fluoren-9-yl)-amide]4-hydroxyamide, 3-(3,4-Dichloro-benzyloxy)-1-methyl-1H-pyrrole-2,4-dicarboxylic acid 4-hydroxyamide 2-[(1,2,3,4-tetrahydro-naphthalen-1-yl)-amide], 3-(3,4-Dichloro-benzyloxy)-1-methyl-1H-pyrrole-2,4-dicarboxylic acid 4- hydroxyamide 2-piperidin-1-ylamide, 3-(3,4-Dichloro-benzyloxy)-1-methyl-1H-pyrrole-2,4-dicarboxylic acid 4-hydroxyamide 2-[(2-hydroxy-indan-1-yl)-amide], 3-(3,4-Dichloro-benzyloxy)-1-methyl-1H-pyrrole-2,4-dicarboxylic acid 2-[(1-benzyl-pyrrolidin-3-yl)-amide]4-hydroxyamide, 3-(3,4-Dichloro-benzyloxy)-1-methyl-1H-pyrrole-2,4-dicarboxylic acid 4-hydroxyamide 2-[(2-hydroxy-indan-1-yl)-amide], 3-(3,4-Dichloro-benzyloxy)-1-methyl-1H-pyrrole-2,4-dicarboxylic acid 2-[(2-carbamoyl-cyclohexyl)-amide]4-hydroxyamide, 3-(3,4-Dichloro-benzyloxy)-1-methyl-1H-pyrrole-2,4-dicarboxylic acid 2-benzylamide 4-hydroxyamide, 3-(3,4-Dichloro-benzyloxy)-1-methyl-1H-pyrrole-2,4-dicarboxylic acid 4-hydroxyamide 2-(2-methoxy-benzylamide), 3-(3,4-Dichloro-benzyloxy)-1-methyl-1H-pyrrole-2,4-dicarboxylic acid 4-hydroxyamide 2-(3-methoxy-benzylamide), 3-(3,4-Dichloro-benzyloxy)-1-methyl-1H-pyrrole-2,4-dicarboxylic acid 2-(2,4-dimethoxy-benzylamide)4-hydroxyamide, 3-(3,4-Dichloro-benzyloxy)-1-methyl-1H-pyrrole-2,4-dicarboxylic acid 2-(3,4-dimethoxy-benzylamide)₄-hydroxyamide, 3-(3,4-Dichloro-benzyloxy)-1-methyl-1H-pyrrole-2,4-dicarboxylic acid 4-hydroxyamide 4-(2,4,6-trimethoxy-benzylamide), 3-(3,4-Dichloro-benzyloxy)-1-methyl-1H-pyrrole-2,4-dicarboxylic acid 4-hydroxyamide 2-{[2-(4-hydroxyphenyl)-ethyl]-amide}, 3-(3,4-Dichloro-benzyloxy)-1-methyl-1H-pyrrole-2,4-dicarboxylic acid 4-hydroxyamide 2-[(pyridin-3-ylmethyl)-amide], 3-(3,4-Dichloro-benzyloxy)-1-methyl-1H-pyrrole-2,4-dicarboxylic acid 4-hydroxyamide 2-[(pyridin-4-ylmethyl)-amide], 3-(3,4-Dichloro-benzyloxy)-1-methyl-1H-pyrrole-2,4-dicarboxylic acid 4-hydroxyamide 2-[(pyridin-2-ylmethyl)-amide], 3-(3,4-Dichloro-benzyloxy)-1-methyl-1H-pyrrole-2,4-dicarboxylic acid 4-hydroxyamide 2-(4-pentyl-benzylamide), 3-(3,4-Dichloro-benzyloxy)-1-methyl-1H-pyrrole-2,4-dicarboxylic acid 4-{[2-(2-chloro-6-fluoro-benzylsulfanyl)-ethyl]-amide}4-hydroxyamide, 3-(3,4-Dichloro-benzyloxy)-1-methyl-1H-pyrrole-2,4-dicarboxylic acid 4-{[2-(2,6-dichloro-benzylsulfanyl)-ethyl]-amide}4-hydroxyamide, 3-(3,4-Dichloro-benzyloxy)-1-methyl-1H-pyrrole-2,4-dicarboxylic acid 2-{[3-(3-acetylamino-phenoxy)-propyl]-amide}4-hydroxyamide, 4-({[3-(3,4-Dichloro-benzyloxy)-4-hydroxycarbamoyl-1-methyl-1H-pyrrole-2-carbonyl]-amino}-methyl)-benzoic acid methyl ester, 3-(3,4-Dichloro-benzyloxy)-1-methyl-1H-pyrrole-2,4-dicarboxylic acid 4-hydroxyamide 2-(4-methyl-benzylamide), 3-(3,4-Dichloro-benzyloxy)-1-methyl-1H-pyrrole-2,4-dicarboxylic acid 4-(2-chloro-6-phenoxy-benzylamide) 4-hydroxyamide, 3-(2,4-Dichloro-benzyloxy)-1-methyl-1H-pyrrole-2,4-dicarboxylic acid 2-(4-dimethylamino-benzylamide)4-hydroxyamide, 3-(2,6-Dichloro-benzyloxy)-1-methyl-1H-pyrrole-2,4-dicarboxylic acid 2-(4-dimethylamino-benzylamide)4-hydroxyamide, 1-Benzyl-3-(3,4-dichloro-benzyloxy)-1H-pyrrole-2,4-dicarboxylic acid 2-[(1-benzyl-piperidin-4-yl)-amide]4-hydroxyamide, 1-Benzyl-3-(3,4-dichloro-benzyloxy)-1H-pyrrole-2,4-dicarboxylic acid 2-[(1-benzyl-piperidin-3-yl)-amide]4-hydroxyamide, 1-Benzyl-3-(3,4-dichloro-benzyloxy)-1H-pyrrole-2,4-dicarboxylic acid 2-{[2-(1-benzyl-piperidin-4-ylamino)-phenyl]-amide}4-hydroxyamide, 3-Benzyloxy-1-methyl-1H-pyrrole-2,4-dicarboxylic acid 4-[(1-benzyl-piperidin-4-yl)-amide]2-hydroxyamide, 3-(4-Methoxy-benzyloxy)-1-methyl-1H-pyrrole-2,4-dicarboxylic acid 4-[(1-benzyl-piperidin-4-yl)-amide]2-hydroxyamide, 3-(3,4-Dichloro-benzyloxy)-1-methyl-1H-pyrrole-2,4-dicarboxylic acid 4-(4-dimethylamino-benzylamide)2-hydroxyamide, 3-(3,4-Dichloro-benzyloxy)-1-methyl-1H-pyrrole-2,4-dicarboxylic acid 4-[(1-benzyl-piperidin-4-yl)-amide]2-hydroxyamide, 3-(3,4-Dichloro-benzyloxy)-1-methyl-1H-pyrrole-2,4-dicarboxylic acid 4-[(1-benzyl-piperidin-3-yl)-amide]2-hydroxyamide, 3-(2,6-Dichloro-benzyloxy)-1-methyl-1H-pyrrole-2,4-dicarboxylic acid 4-[(1-benzyl-piperidin-4-yl)-amide]2-hydroxyamide, 3-(2,6-Dichloro-benzyloxy)-1-methyl-1H-pyrrole-2,4-dicarboxylic acid 4-[(1-benzyl-piperidin-3-yl)-amide]2-hydroxyamide, 3-(4-Cyano-benzyloxy)-1-methyl-1H-pyrrole-2,4-dicarboxylic acid 4-[(1-benzyl-piperidin-3-yl)-amide]2-hydroxyamide, 3-(4-Cyano-benzyloxy)-1-methyl-1H-pyrrole-2,4-dicarboxylic acid 4-[(1-benzyl-piperidin-4-yl)-amide]2-hydroxyamide, 1-Methyl-3-(pyridin-4-ylmethoxy)-1H-pyrrole-2,4-dicarboxylic acid 4-[(1-benzyl-piperidin-4-yl)-amide]2-hydroxyamide, 1-Methyl-3-(pyridin-4-ylmethoxy)-1H-pyrrole-2,4-dicarboxylic acid 4-[(1-benzyl-piperidin-3-yl)-amide]2-hydroxyamide, or, 3-(3,4-Difluoro-benzyloxy)-1-methyl-1H-pyrrole-2,4-dicarboxylic acid 4-[(1-benzyl-piperidin-4-yl)-amide]2-hydroxyamide.

22. The compound of claim 1 having the structure

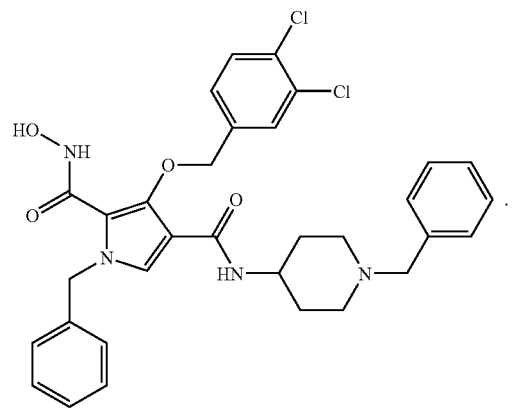

* * * * *